US011744635B2

(12) United States Patent
Madan et al.

(10) Patent No.: US 11,744,635 B2
(45) Date of Patent: Sep. 5, 2023

(54) STERILE MEDICAL INSTRUMENT CHARGING DEVICE

(71) Applicant: Cilag GmbH International, Zug (CH)

(72) Inventors: Ashvani K. Madan, Mason, OH (US); Donna L. Korvick, San Antonio, TX (US); Aron O. Zingman, Cambridge, MA (US); John W. Willis, Milford, OH (US); Kevin L. Houser, Springboro, OH (US); Gavin M. Monson, Oxford, OH (US); Kevin D. Felder, Cincinnati, OH (US); Michael J. Stokes, Cincinnati, OH (US); Sora Rhee, Pennsylvania Furnace, PA (US); Timothy G. Dietz, Reading, MA (US); Jeffrey L. Aldridge, Lebanon, OH (US)

(73) Assignee: Cilag GmbH International, Zug (CH)

( * ) Notice: Subject to any disclaimer, the term of this patent is extended or adjusted under 35 U.S.C. 154(b) by 308 days.

(21) Appl. No.: 16/779,748

(22) Filed: Feb. 3, 2020

(65) Prior Publication Data

US 2020/0229863 A1 Jul. 23, 2020

Related U.S. Application Data

(63) Continuation of application No. 15/212,423, filed on Jul. 18, 2016, now Pat. No. 10,660,695, which is a
(Continued)

(51) Int. Cl.
*A61B 18/14* (2006.01)
*A61B 90/40* (2016.01)
(Continued)

(52) U.S. Cl.
CPC .... *A61B 18/1442* (2013.01); *A61B 17/00234* (2013.01); *A61B 17/2812* (2013.01);
(Continued)

(58) Field of Classification Search
CPC ............ A61B 17/00234; A61B 17/064; A61B 17/2812; A61B 17/285; A61B 17/320092;
(Continued)

(56) References Cited

U.S. PATENT DOCUMENTS

| 1,754,806 A | 4/1930 | Stevenson |
| 3,297,192 A | 1/1967 | Swett |

(Continued)

FOREIGN PATENT DOCUMENTS

| CN | 101683281 A | 3/2010 |
| CN | 101819334 A | 4/2013 |

(Continued)

OTHER PUBLICATIONS

Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
(Continued)

*Primary Examiner* — Khadijeh A Vahdat
(74) *Attorney, Agent, or Firm* — Frost Brown Todd LLP

(57) ABSTRACT

A system includes a medical device and a charging device. A sterile barrier may be interposed between the medical device and the charging device. The medical device includes an integral power source and an active element. The charging device is configured to charge the integral power source. The charging device may charge the integral power source through direct contact between features of the charging device and features the medical device. The charging device may alternatively charge the integral power source wirelessly, such as through inductive coupling. The medical device may include conductive prongs that are retained by the charging device. The charging device may physically couple with the medical device via magnets. The medical device and the charging device may be provided together in
(Continued)

a sterile package as a kit. The kit may also include a reclamation bag to facilitate reclamation of electrical components.

20 Claims, 12 Drawing Sheets

Related U.S. Application Data continuation of application No. 13/151,503, filed on Jun. 2, 2011, now Pat. No. 9,597,143.

(60) Provisional application No. 61/487,846, filed on May 19, 2011, provisional application No. 61/410,603, filed on Nov. 5, 2010.

(51) Int. Cl.

| | | |
|---|---|---|
| *A61B 18/00* | (2006.01) | |
| *A61B 18/04* | (2006.01) | |
| *A61B 18/12* | (2006.01) | |
| *H02J 50/10* | (2016.01) | |
| *A61B 17/32* | (2006.01) | |
| *G16H 40/63* | (2018.01) | |
| *G16H 20/40* | (2018.01) | |
| *A61B 50/30* | (2016.01) | |
| *A61B 34/00* | (2016.01) | |
| *A61B 46/10* | (2016.01) | |
| *A61B 17/00* | (2006.01) | |
| *A61B 17/28* | (2006.01) | |
| *A61N 7/00* | (2006.01) | |
| *H01M 10/46* | (2006.01) | |
| *H01M 10/48* | (2006.01) | |
| *H02J 7/00* | (2006.01) | |
| *A61B 17/064* | (2006.01) | |
| *A61B 17/285* | (2006.01) | |
| *A61B 17/29* | (2006.01) | |
| *A61B 50/33* | (2016.01) | |
| *A61B 50/00* | (2016.01) | |
| *A61B 90/00* | (2016.01) | |

(52) U.S. Cl.
CPC ...... *A61B 17/320092* (2013.01); *A61B 18/00* (2013.01); *A61B 18/04* (2013.01); *A61B 18/12* (2013.01); *A61B 18/14* (2013.01); *A61B 18/1445* (2013.01); *A61B 34/25* (2016.02); *A61B 46/10* (2016.02); *A61B 50/30* (2016.02); *A61B 90/40* (2016.02); *A61N 7/00* (2013.01); *G16H 20/40* (2018.01); *G16H 40/63* (2018.01); *H01M 10/46* (2013.01); *H01M 10/48* (2013.01); *H02J 7/0044* (2013.01); *H02J 7/0045* (2013.01); *H02J 50/10* (2016.02); *A61B 17/064* (2013.01); *A61B 17/285* (2013.01); *A61B 18/1206* (2013.01); *A61B 18/1233* (2013.01); *A61B 50/33* (2016.02); *A61B 90/08* (2016.02); *A61B 2017/0046* (2013.01); *A61B 2017/00084* (2013.01); *A61B 2017/0084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2017/320069* (2017.08); *A61B 2017/320071* (2017.08); *A61B 2017/320094* (2017.08); *A61B 2017/320095* (2017.08); *A61B 2018/0019* (2013.01); *A61B 2018/00178* (2013.01); *A61B 2018/00589* (2013.01); *A61B 2018/00595* (2013.01); *A61B 2018/00601* (2013.01); *A61B 2018/00607* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2050/0065* (2016.02); *A61B 2050/3008* (2016.02); *A61B 2090/0803* (2016.02); *A61B 2090/0813* (2016.02); *A61B 2090/0814* (2016.02); *H01M 2220/30* (2013.01); *H02J 7/0048* (2020.01); *Y10T 29/49005* (2015.01); *Y10T 29/49895* (2015.01); *Y10T 29/53913* (2015.01)

(58) Field of Classification Search
CPC ......... A61B 18/00; A61B 18/04; A61B 18/12; A61B 18/1206; A61B 18/1233; A61B 18/14; A61B 18/1442; A61B 18/1445; A61B 2017/00084; A61B 2017/00398; A61B 2017/0046; A61B 2017/00473; A61B 2017/00477; A61B 2017/00482; A61B 2017/00734; A61B 2017/0084; A61B 2017/291; A61B 2017/2929; A61B 2017/293; A61B 2017/2931; A61B 2017/2933; A61B 2017/294; A61B 2017/320069; A61B 2017/320071; A61B 2017/320094; A61B 2017/320095; A61B 2018/00178; A61B 2018/0019; A61B 2018/00589; A61B 2018/00595; A61B 2018/00601; A61B 2018/00607; A61B 2018/00791; A61B 2018/00988; A61B 2018/1226; A61B 2018/1412; A61B 2018/1455; A61B 2050/0065; A61B 2050/3008; A61B 2090/0803; A61B 2090/0813; A61B 2090/0814; A61B 34/25; A61B 46/10
USPC .................................................. 606/33–50
See application file for complete search history.

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,641,077 A | 2/1987 | Pascaloff |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. et al. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,308,358 A | 5/1994 | Bond et al. |

(56) References Cited

U.S. PATENT DOCUMENTS

| | | |
|---|---|---|
| 5,322,055 A | 6/1994 | Davison et al. |
| 5,339,799 A | 8/1994 | Kami et al. |
| 5,357,732 A | 10/1994 | Markle et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,452,391 A | 9/1995 | Chou et al. |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,371 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,893,835 A | 4/1999 | Witt et al. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,113,596 A | 9/2000 | Hooven et al. |
| 6,123,702 A | 9/2000 | Swanson et al. |
| 6,165,191 A | 12/2000 | Shibata et al. |
| 6,190,386 B1 | 2/2001 | Rydell |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,512,667 B2 | 1/2003 | Shiue et al. |
| 6,514,267 B2 | 2/2003 | Jewett |
| 6,517,561 B1 | 2/2003 | Phillips |
| 6,520,185 B1 | 2/2003 | Bommannan et al. |
| 6,561,983 B2 | 5/2003 | Cronin et al. |
| 6,562,032 B1 | 5/2003 | Ellman et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,091 B1 | 11/2003 | Shiue et al. |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,706,038 B2 | 3/2004 | Francischelli et al. |
| 6,717,193 B2 | 4/2004 | Olewine et al. |
| 6,730,042 B2 | 5/2004 | Fulton et al. |
| 6,753,673 B2 | 6/2004 | Shiue et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,836,097 B2 | 12/2004 | Turner et al. |
| 6,838,862 B2 | 1/2005 | Luu |
| 6,847,192 B2 | 1/2005 | Turner et al. |
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 6,998,822 B2 | 2/2006 | Turner et al. |
| 7,031,155 B2 | 4/2006 | Sauciuc et al. |
| 7,061,749 B2 | 6/2006 | Liu et al. |
| 7,077,853 B2 | 7/2006 | Kramer et al. |
| 7,083,589 B2 | 8/2006 | Banko et al. |
| 7,085,123 B2 | 8/2006 | Shiue et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,160,132 B2 | 1/2007 | Phillips et al. |
| 7,169,146 B2 | 1/2007 | Truckai et al. |
| 7,186,253 B2 | 3/2007 | Truckai et al. |
| 7,186,473 B2 | 3/2007 | Shiue et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger et al. |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,353,068 B2 | 4/2008 | Tanaka et al. |
| 7,354,440 B2 | 4/2008 | Truckai et al. |
| 7,364,061 B2 | 4/2008 | Swayze et al. |
| 7,364,554 B2 | 4/2008 | Bolze et al. |
| 7,375,644 B2 | 5/2008 | Miyazawa |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,470,237 B2 | 12/2008 | Beckman et al. |
| 7,473,145 B2 | 1/2009 | Her et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,560,903 B2 | 7/2009 | Thrap |
| 7,563,142 B1 | 7/2009 | Wenger et al. |
| 7,570,994 B2 | 8/2009 | Tamura et al. |
| 7,573,151 B2 | 8/2009 | Acena et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,658,247 B2 | 2/2010 | Carter |
| 7,692,411 B2 | 4/2010 | Trainor et al. |
| 7,699,850 B2 | 4/2010 | Miller |
| 7,699,856 B2 | 4/2010 | Van Wyk et al. |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,761,198 B2 | 7/2010 | Bhardwaj |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton, IV et al. |
| 7,776,037 B2 | 8/2010 | Odom |
| 7,780,660 B2 | 8/2010 | Bourne et al. |

(56) References Cited

U.S. PATENT DOCUMENTS

| | | |
|---|---|---|
| 7,802,121 B1 | 9/2010 | Zansky et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,918,848 B2 | 4/2011 | Lau et al. |
| 7,922,063 B2 | 4/2011 | Zemlok et al. |
| 7,923,151 B2 | 4/2011 | Lam et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 7,977,921 B2 | 7/2011 | Bahai et al. |
| 7,982,439 B2 | 7/2011 | Trainor et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,083,120 B2 | 12/2011 | Shelton et al. |
| 8,097,011 B2 | 1/2012 | Hideo et al. |
| 8,142,461 B2 | 3/2012 | Houser et al. |
| 8,147,488 B2 | 4/2012 | Masuda |
| 8,177,776 B2 | 5/2012 | Humayun et al. |
| 8,179,103 B2 | 5/2012 | Doljack |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,323,271 B2 | 12/2012 | Humayun et al. |
| 8,328,732 B2 | 12/2012 | Parihar et al. |
| 8,328,802 B2 | 12/2012 | Deville et al. |
| 8,333,764 B2 | 12/2012 | Francischelli et al. |
| 8,336,725 B2 | 12/2012 | Ramsey et al. |
| 8,337,097 B2 | 12/2012 | Cao |
| 8,344,690 B2 | 1/2013 | Smith et al. |
| 8,372,099 B2 | 2/2013 | Deville et al. |
| 8,377,059 B2 | 2/2013 | Deville et al. |
| 8,400,108 B2 | 3/2013 | Powell et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,419,757 B2 | 4/2013 | Smith et al. |
| 8,419,758 B2 | 4/2013 | Smith et al. |
| 8,425,545 B2 | 4/2013 | Smith et al. |
| 8,444,653 B2 | 5/2013 | Nycz et al. |
| 8,444,662 B2 | 5/2013 | Palmer et al. |
| 8,449,529 B2 | 5/2013 | Bek et al. |
| 8,459,520 B2 | 6/2013 | Giordano et al. |
| 8,461,744 B2 | 6/2013 | Wiener et al. |
| 8,487,487 B2 | 7/2013 | Dietz et al. |
| 8,522,795 B2 | 9/2013 | Bouix et al. |
| 8,550,106 B2 | 10/2013 | Hebach et al. |
| 8,550,981 B2 | 10/2013 | Woodruff et al. |
| 8,551,088 B2 | 10/2013 | Falkenstein et al. |
| 8,564,242 B2 | 10/2013 | Hansford et al. |
| 8,573,461 B2 | 11/2013 | Shelton et al. |
| 8,574,253 B2 | 11/2013 | Gruber et al. |
| 8,598,852 B2 | 12/2013 | Gilmore |
| 8,602,287 B2 | 12/2013 | Laurent et al. |
| 8,608,045 B2 | 12/2013 | Smith et al. |
| 8,617,077 B2 | 12/2013 | van Groningen et al. |
| 8,622,274 B2 | 1/2014 | Yates et al. |
| 8,623,027 B2 | 1/2014 | Price et al. |
| 8,632,535 B2 | 1/2014 | Shelton, IV et al. |
| 8,636,736 B2 | 1/2014 | Yates et al. |
| 8,641,629 B2 | 2/2014 | Kurokawa |
| 8,657,174 B2 | 2/2014 | Yates et al. |
| 8,663,112 B2 | 3/2014 | Slayton et al. |
| 8,733,614 B2 | 5/2014 | Ross et al. |
| 8,758,342 B2 | 6/2014 | Bales et al. |
| 8,784,415 B2 | 7/2014 | Malackowski et al. |
| 8,808,319 B2 | 8/2014 | Houser et al. |
| 8,834,465 B2 | 9/2014 | Ramstein et al. |
| 8,864,761 B2 | 10/2014 | Johnson et al. |
| 8,906,017 B2 | 12/2014 | Rioux et al. |
| 8,939,974 B2 | 1/2015 | Boudreaux et al. |
| 8,961,441 B2 | 2/2015 | Cioanla et al. |
| 8,968,648 B2 | 3/2015 | Kaneko |
| 8,986,302 B2 | 3/2015 | Boudreaux et al. |
| 8,998,939 B2 | 4/2015 | Price et al. |
| 9,000,720 B2 | 4/2015 | Stulen et al. |
| 9,011,336 B2 | 4/2015 | Slayton et al. |
| 9,011,427 B2 | 4/2015 | Price et al. |
| 9,011,471 B2 | 4/2015 | Timm et al. |
| 9,017,849 B2 | 4/2015 | Stulen et al. |
| 9,017,851 B2 | 4/2015 | Felder et al. |
| 9,023,071 B2 | 5/2015 | Miller et al. |
| 9,039,720 B2 | 5/2015 | Madan |
| 9,044,261 B2 | 6/2015 | Houser |
| 9,050,098 B2 | 6/2015 | Deville et al. |
| 9,050,125 B2 | 6/2015 | Boudreaux et al. |
| 9,060,750 B2 | 6/2015 | Lam |
| 9,072,523 B2 | 7/2015 | Houser et al. |
| 9,072,543 B2 | 7/2015 | Miller et al. |
| 9,078,671 B2 | 7/2015 | Beale et al. |
| 9,089,338 B2 | 7/2015 | Smith et al. |
| 9,095,346 B2 | 8/2015 | Houser et al. |
| 9,113,903 B2 | 8/2015 | Unger |
| 9,161,803 B2 | 10/2015 | Yates et al. |
| 9,179,912 B2 | 11/2015 | Yates et al. |
| 9,186,046 B2 | 11/2015 | Ramamurthy et al. |
| 9,186,047 B2 | 11/2015 | Ramamurthy et al. |
| 9,192,428 B2 | 11/2015 | Houser et al. |
| 9,247,986 B2 | 2/2016 | Haberstich et al. |
| 9,308,009 B2 | 4/2016 | Madan et al. |
| 9,318,271 B2 | 4/2016 | Fletcher et al. |
| 9,364,279 B2 | 6/2016 | Houser et al. |
| 9,364,288 B2 | 6/2016 | Smith et al. |
| 9,375,255 B2 | 6/2016 | Houser et al. |
| 9,381,058 B2 | 7/2016 | Houser et al. |
| 9,408,575 B2 | 8/2016 | Bordoley et al. |
| 9,820,738 B2 | 11/2017 | Lytle et al. |
| 10,004,497 B2 | 6/2018 | Overmyer et al. |
| 10,376,304 B2 | 8/2019 | Houser et al. |
| 10,537,380 B2 | 1/2020 | Houser et al. |
| 2001/0032666 A1 | 10/2001 | Jenson et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2003/0144680 A1 | 7/2003 | Kellogg et al. |
| 2003/0216723 A1* | 11/2003 | Shinmura ............ A61B 90/25 606/34 |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0171522 A1 | 8/2005 | Christopherson |
| 2005/0203546 A1 | 9/2005 | Van Wyk et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0078484 A1 | 4/2007 | Talarico et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |

(56) References Cited

U.S. PATENT DOCUMENTS

| | | |
|---|---|---|
| 2007/0265620 A1 | 11/2007 | Kraas et al. |
| 2007/0282333 A1 | 12/2007 | Fortson et al. |
| 2007/0290654 A1* | 12/2007 | Govari .................. H02J 7/0044 |
| | | 320/155 |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0164842 A1 | 7/2008 | Bergner |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0228104 A1 | 9/2008 | Uber, II et al. |
| 2008/0255413 A1 | 10/2008 | Zemlok et al. |
| 2008/0281301 A1 | 11/2008 | Deboer et al. |
| 2008/0315829 A1 | 12/2008 | Jones et al. |
| 2009/0043797 A1 | 2/2009 | Dorie et al. |
| 2009/0076506 A1 | 3/2009 | Baker |
| 2009/0096430 A1 | 4/2009 | Van Der Linde et al. |
| 2009/0143799 A1 | 6/2009 | Smith et al. |
| 2009/0143800 A1 | 6/2009 | Deville et al. |
| 2009/0253030 A1 | 10/2009 | Kooij |
| 2009/0281430 A1 | 11/2009 | Wilder |
| 2010/0021022 A1 | 1/2010 | Pittel et al. |
| 2010/0030218 A1 | 2/2010 | Prevost |
| 2010/0060231 A1 | 3/2010 | Trainor et al. |
| 2010/0076455 A1 | 3/2010 | Birkenbach et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0145146 A1 | 6/2010 | Melder |
| 2010/0152610 A1 | 6/2010 | Parihar et al. |
| 2010/0201311 A1 | 8/2010 | Alexander et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2011/0009694 A1 | 1/2011 | Schultz et al. |
| 2011/0074336 A1 | 3/2011 | Miller |
| 2011/0077514 A1 | 3/2011 | Ulric et al. |
| 2011/0080134 A1 | 4/2011 | Miller |
| 2011/0121049 A1 | 5/2011 | Malinouskas et al. |
| 2011/0181238 A1* | 7/2011 | Soar ...................... H01F 27/366 |
| | | 320/108 |
| 2011/0221398 A1 | 9/2011 | Ferber |
| 2012/0111591 A1 | 5/2012 | Shelton, IV et al. |
| 2012/0116260 A1 | 5/2012 | Johnson et al. |
| 2012/0116261 A1 | 5/2012 | Mumaw et al. |
| 2012/0116262 A1 | 5/2012 | Houser et al. |
| 2012/0116263 A1 | 5/2012 | Houser et al. |
| 2012/0116265 A1 | 5/2012 | Houser et al. |
| 2012/0116266 A1 | 5/2012 | Houser et al. |
| 2012/0116267 A1 | 5/2012 | Kimball et al. |
| 2012/0116366 A1 | 5/2012 | Houser et al. |
| 2012/0116380 A1 | 5/2012 | Madan et al. |
| 2012/0116381 A1 | 5/2012 | Houser et al. |
| 2012/0116388 A1 | 5/2012 | Houser et al. |
| 2012/0116389 A1 | 5/2012 | Houser et al. |
| 2012/0116391 A1 | 5/2012 | Houser et al. |
| 2012/0179036 A1 | 7/2012 | Patrick et al. |
| 2012/0292367 A1 | 11/2012 | Morgan et al. |
| 2012/0305427 A1 | 12/2012 | Felder et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090552 A1 | 4/2013 | Ramamurthy et al. |
| 2013/0090675 A1 | 4/2013 | Mumaw et al. |
| 2013/0118733 A1 | 5/2013 | Kumar |
| 2014/0088739 A1 | 3/2014 | Ellis et al. |
| 2015/0305763 A1 | 10/2015 | Houser et al. |
| 2016/0121143 A1 | 5/2016 | Mumaw et al. |
| 2016/0206900 A1 | 7/2016 | Haberstich et al. |
| 2016/0329614 A1 | 11/2016 | Madan et al. |
| 2016/0338760 A1 | 11/2016 | Houser et al. |
| 2017/0245913 A1 | 8/2017 | Houser et al. |
| 2018/0055559 A1 | 3/2018 | Shelton, IV et al. |

FOREIGN PATENT DOCUMENTS

| | | |
|---|---|---|
| DE | 102008051866 | 10/2010 |
| DE | 102009013034 | 10/2010 |
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | H 01-268370 | 10/1989 |
| JP | H 10-308907 | 11/1998 |
| JP | 2002-336265 | 11/2002 |
| JP | 2005-033868 | 2/2005 |
| JP | 2010-518978 | 6/2010 |
| JP | 5410110 B | 2/2014 |
| WO | WO 1997/024072 | 7/1997 |
| WO | WO 2000/065682 | 2/2000 |
| WO | WO 2003/013374 | 2/2003 |
| WO | WO 2003/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/050439 | 5/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

"System 6 Aseptic Battery System," Stryker (2006) pp. 1-2.

Australian First Examination Report dated May 18, 2015 for Application No. 2011323284.

Chinese Office Action dated Jan. 29, 2015 for Application No. 2011800640106.

Chinese Office Action dated Jan. 29, 2015 for Application No. 2011800638159.

Chinese Office Action dated Feb. 2, 2015 for Application No. 2011800534501.

Chinese First Office Action dated Feb. 2, 2015 for App. No. CN 2011800641490.

(56) References Cited

OTHER PUBLICATIONS

Chinese First Office Action dated Feb. 16, 2015 for App. No. CN 2011800638356.
Chinese Office Action dated Feb. 16, 2015 for Application No. 2011800638286.
Chinese First Office Action dated Feb. 28, 2015 for App No. CN 2011800641471.
Chinese Office Action dated Mar. 4, 2015 for Application No. 201180063595.X.
Chinese Office Action dated Mar. 30, 2015 for Application No. 2011800639823.
Chinese Office Action dated Mar. 27, 2015 for Application No. 2011800638214.
Chinese First Office Action dated Apr. 16, 2015 for App. No. CN 201180063919X.
Chinese Office Action dated Apr. 20, 2015 for Application No. 2011800534342.
Chinese Office Action dated Oct. 8, 2016 for Application No. 2011800534342.
Chinese Search Report dated Oct. 8, 2016 for App. No. CN 2011800534342.
Chinese Third Office Action dated Oct. 17, 2016 for App. No. CN 2011800534342.
Chinese Office Action dated 17/17/16 for Application No. 2011800534342.
Chinese Office Action dated Aug. 28, 2015 for Application No. 2011800640106.
EP Communication dated Feb. 19, 2014 for Application No. EP 11781972.2.
Indian Office Action, Examination Report, dated Mar. 28, 2018 for Application No. 4008/DELNP/2013, 6 pgs.
Indian Office Action, Examination Report, dated Jun. 13, 2019 for Application No. 3973/DELNP/2013, 6 pgs.
International Search Report and Written Opinion dated Jan. 26, 2012for Application No. PCT/US2011/059212.
International Preliminary Report on Patentability dated May 7, 2013 for Application No. PCT/US2011/059212.
Communication from International Searching Authority dated Jan. 24, 2012 for Application No. PCT/US2011/059215.
International Search Report dated Apr. 4, 2012 for Application No. PCT/US2011/059215.
International Preliminary Report on Patentability dated May 8, 2013 for Application No. PCT/US2011/059215.
International Search Report dated Feb. 13, 2012for Application No. PCT/US2011/059217.
International Preliminary Report on Patentability dated May 7, 2013 for Application No. PCT/US2011/059217.
International Search Report dated Jun. 12, 2012 for Application No. PCT/US2011/059218.
International Preliminary Report on Patentability dated May 7, 2013 for Application No. PCY/US2011/059218.
International Search Report dated Jan. 26, 2012 for Application No. PCT/US11/059220.
International Preliminary Report on Patentability dated May 7, 2013 for Application No. PCT/US2011/059220.
Communication from International Searching Authority dated Feb. 2, 2012for Application No. PCT/US2011/059222.
International Search Report dated Apr. 18, 2012 for Application No. PCT/US2011/059222.
International Preliminary Report on Patentability dated May 7, 2013 for Application No. PCT/US2011/059222.
International Search Report dated Feb. 1, 2012 for Application No. PCT/US11/059223.
International Preliminary Report on Patentability dated Feb. 1, 2012 for Application No. PCT/US2011/059223.
International Search Report dated Jan. 12, 2012 for Application No. PCT/US11/059226.
International Preliminary Report on Patentability dated May 7, 2013 for Application No. PCT/US2011/059226.
International Search Report dated Mar. 15, 2012 for Application No. PCT/US2011/059338.
International Preliminary Report on Patentability dated May 7, 2013 for Application No. PCT/US2011/059338.
International Search Report dated Feb. 7, 2012 for Application No. PCT/US2011/059351.
International Preliminary Report on Patentability dated May 7, 2013 for Application No. PCT/US2011/059351.
International Search Report dated Feb. 2, 2012for Application No. PCT/US2011/059354.
International Preliminary Report on Patentability dated May 7, 2013 for Application No. PCT/US2011/059354.
International Search Report dated May 29, 2012 for Application No. PCT/US11/059358.
International Preliminary Report on Patentability dated May 7, 2013 for Application No. PCT/US2011/059358.
Communication from International Searching Authority dated Feb. 6, 2012for Application No. PCT/US2011/059362.
International Search Report dated Aug. 22, 2012for Application No. PCT/US2011/059362.
International Preliminary Report on Patentability dated May 7, 2013 for Application No. PCT/US2011/059362.
International Search Report dated Jun. 4, 2012 for Application No. PCT/US2011/059365.
International Preliminary Report on Patentability dated May 8, 2013 for Application No. PCT/US2011/059365.
International Search Report dated Feb. 23, 2012 for Application No. PCT/US2011/059371.
International Preliminary Report on Patentability dated May 7, 2013 for Application No. PCT/US2011/059371.
Communication from International Searching Authority dated Feb. 2, 2012 for Application No. PCT/US2011/059378.
International Search Report dated May 24, 2012 for Application No. PCT/US2011/059378.
International Search Report and Written Opinion dated Feb. 2, 2012for Application No. PCT/US2011/059378.
International Preliminary Report on Patentability dated May 7, 2013 for Application No. PCT/US2011/059378.
International Search Report dated Apr. 11, 2012 for Application No. PCT/US2011/059381.
International Search Report and Written Opinion dated Jul. 6, 2012 for PCT/US2011/059381.
International Preliminary Report on Patentability dated May 8, 2013 for Application No. PCT/US2011/059381.
Japanese Office Action, Notification of Reasons for Refusal, dated Sep. 1, 2015 for Application No. 2013-537837.
Japanese Office Action, Notification of Reasons for Refusal, dated Feb. 16, 2016 for Application No. 2013-537837.
Japanese Office Action, Pretrial Examination Report, dated Aug. 2, 2016 for Application No. 2013-537837.
Japanese Office Action, Notification of Reasons for Refusal, dated Sep. 1, 2015 for Application No. 2013-537866.
Japanese Office Action, Notification of Reasons for Refusal, dated Jun. 28, 2016 for Application No. 2013-537866.
Japanese Office Action, Examiner's Decision of Refusal, dated Sep. 13, 2016 for Application No. 2013-537869.
Japanese Office Action, Notification of Reasons for Refusal, dated Oct. 6, 2015 for Application No. 2013-537869.
Office Action Non-Final dated Aug. 6, 2013 for U.S. Appl. No. 13/151,471.
Notice of Allowance dated Dec. 6, 2013 for U.S. Appl. No. 13/151,471.
Office Action Non-Final dated Mar. 28, 2014 for U.S. Appl. No. 13/151,471.
U.S. Office Action, Notice of Allowance, dated Aug. 19, 2014 for U.S. Appl. No. 13/151,471.
U.S. Office Action, Notice of Allowance, dated Nov. 21, 2014 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.

(56) References Cited

OTHER PUBLICATIONS

U.S. Office Action, Non-Final, dated Aug. 14, 2014 for U.S. Appl. No. 13/151,481.
U.S. Office Action, Final, dated Apr. 1, 2015 for U.S. Appl. No. 13/151,481.
U.S. Office Action, Notice of Allowance, dated Jun. 10, 2015 for U.S. Appl. No. 13/151,481.
Restriction Requirement dated Jul. 5, 2013 for U.S. Appl. No. 13/151,488.
U.S. Office Action, Non-Final, dated Nov. 7, 2014 for U.S. Appl. No. 13/151,488.
U.S. Office Action, Final, dated Jul. 17, 2015 for U.S. Appl. No. 13/151,488.
Office Action Non-Final dated Jun. 14, 2013 for U.S. Appl. No. 13/151,498.
Office Action Final dated Nov. 21, 2013 for U.S. Appl. No. 13/151,498.
Office Action Non-Final dated Mar. 18, 2014 for U.S. Appl. No. 13/151,498.
U.S. Office Action, Notice of Allowance, dated Aug. 6, 2014 for U.S. Appl. No. 13/151,498.
U.S. Office Action, Notice of Allowance, dated Nov. 21, 2014 for U.S. Appl. No. 13/151,498.
U.S. Office Action, Non-Final, dated Jun. 18, 2014 for U.S. Appl. No. 13/151,503.
U.S. Office Action, Non-Final, dated Nov. 6, 2014 for U.S. Appl. No. 13/151,503.
U.S. Office Action, Final, dated Jun. 8, 2015 for U.S. Appl. No. 13/151,503.
U.S. Office Action, Non-Final, dated Oct. 2, 2015 for U.S. Appl. No. 13/151,503.
U.S. Office Action, Final, dated Mar. 9, 2016 for U.S. Appl. No. 13/151,503.
U.S. Office Action, Notice of Allowance, dated Jul. 27, 2016 for U.S. Appl. No. 13/151,503.
U.S. Office Action, Notice of Allowance, dated Nov. 2, 2016 for U.S. Appl. No. 13/151,503.
Restriction Requirement dated Mar. 13, 2013 for U.S. Appl. No. 13/151,509.
Restriction Requirement dated Jun. 24, 2013 for U.S. Appl. No. 13/151,509.
Office Action Non-Final dated Sep. 26, 2013 for U.S. Appl. No. 13/151,509.
Office Action Final dated Jan. 29, 2014 for U.S. Appl. No. 13/151,509.
Office Action Non-Final dated Jul. 9, 2014 for U.S. Appl. No. 13/151,509.
U.S. Office Action, Notice of Allowance, dated Oct. 28, 2014 for U.S. Appl. No. 13/151,509.
U.S. Office Action, Notice of Allowance, dated Feb. 25, 2015 for U.S. Appl. No. 13/151,509.
Restriction Requirement dated Jun. 11, 2014 for U.S. Appl. No. 13/151,512.
U.S. Office Action, Notice of Allowance, dated Oct. 29, 2014 for U.S. Appl. No. 13/151,512.
U.S. Office Action, Notice of Allowance, dated Feb. 17, 2015 for U.S. Appl. No. 13/151,512.
U.S. Office Action, Restriction Requirement, dated Jul. 11, 2014 for U.S. Appl. No. 13/269,870.
U.S. Office Action, Non-Final, dated Jan. 5, 2015 for U.S. Appl. No. 13/269,870.
Restriction Requirement dated Feb. 28, 2013 for U.S. Appl. No. 13/270,667.
Office Action Non-Final dated Apr. 26, 2013 for U.S. Appl. No. 13/270,667.
Office Action Final dated Oct. 25, 2013 for U.S. Appl. No. 13/270,667.
U.S. Office Action, Non-Final, dated Jul. 29, 2014 for U.S. Appl. No. 13/270,667.
U.S. Office Action, Notice of Allowance, dated Dec. 17, 2014 for U.S. Appl. No. 13/270,667.
U.S. Office Action, Restriction Requirement, dated Jul. 9, 2014 for U.S. Appl. No. 13/270,684.
U.S. Office Action, Non-Final, dated Oct. 9, 2014 for U.S. Appl. No. 13/270,684.
U.S. Office Action, Final, dated Mar. 7, 2015 for U.S. Appl. No. 13/270,684.
U.S. Office Action, Notice of Allowance, dated Jul. 28, 2015 for U.S. Appl. No. 13/270,684.
U.S. Office Action, Restriction Requirement, dated Sep. 11, 2014 for U.S. Appl. No. 13/270,701.
U.S. Office Action, Non-Final, dated Dec. 16, 2014 for U.S. Appl. No. 13/270,701.
U.S. Office Action, Final, dated Jun. 17, 2015 for U.S. Appl. No. 13/270,701.
Office Action Non-Final dated Nov. 21, 2013 for U.S. Appl. No. 13/271,352.
U.S. Office Action, Restriction Requirement, dated Sep. 25, 2014 for U.S. Appl. No. 13/271,352.
U.S. Office Action, Non-Final, dated Mar. 26, 2015 for U.S. Appl. No. 13/271,352.
U.S. Office Action, Final, dated Jul. 15, 2015 for U.S. Appl. No. 13/271,352.
U.S. Office Action, Restriction Requirement, dated Feb. 25, 2015 for U.S. Appl. No. 13/271,364.
U.S. Office Action, Non-Final, dated Jul. 14, 2015 for U.S. Appl. No. 13/271,364.
U.S. Office Action, Restriction Requirement, dated Oct. 2, 2013 for U.S. Appl. No. 13/274,480.
Office Action Non-Final dated Feb. 14, 2014 for U.S. Appl. No. 13/274,480.
U.S. Office Action, Final, dated Jul. 17, 2014 for U.S. Appl. No. 13/274,480.
U.S. Office Action, Non-Final, dated May 1, 2015 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
U.S. Office Action, Final, dated Aug. 22, 2014 for U.S. Appl. No. 13/274,496.
U.S. Office Action, Non-Final, dated Apr. 2, 2015 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
U.S. Office Action, Non-Final, dated Jul. 22, 2015 for U.S. Appl. No. 13/274,507.
Office Action Non-Final dated Dec. 21, 2012 for U.S. Appl. No. 13/274,516.
Office Action Final dated Aug. 16, 2013 for U.S. Appl. No. 13/274,516.
Office Action Non-Final dated Dec. 6, 2013 for U.S. Appl. No. 13/274,516.
U.S. Office Action, Final, dated Jun. 12, 2014 for U.S. Appl. No. 13/274,516.
U.S. Office Action, Non-Final, dated Oct. 8, 2014 for U.S. Appl. No. 13/274,516.
U.S. Office Action, Final, dated May 8, 2015 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Final dated Oct. 25, 2013 for U.S. Appl. No. 13/274,540.
U.S. Office Action. Non-Final, dated Aug. 26, 2014 for U.S. Appl. No. 13/274,540.
U.S. Office Action, Notice of Allowance, dated Jan. 21, 2015 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.

(56) References Cited

OTHER PUBLICATIONS

U.S. Office Action, Non-Final, dated Aug. 14, 2014 for U.S. Appl. No. 13/274,805.
U.S. Office Action, Notice of Allowance, dated Nov. 28, 2014 for U.S. Appl. No. 13/274,805.
U.S. Office Action, Notice of Allowance, dated Jan. 21, 2015 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Office Action Final dated Nov. 26, 2013 for U.S. Appl. No. 13/274,830.
U.S. Office Action, Non-Final, dated Oct. 22, 2014 for U.S. Appl. No. 13/274,830.
U.S. Office Action, Notice of Allowance, dated Mar. 23, 2015 for U.S. Appl. No. 13/274,830.
U.S. Office Action, Notice of Allowance, dated Jul. 9, 2015 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Final dated Dec. 5, 2013 for U.S. Appl. No. 13/275,495.
U.S. Office Action, Non-Final, dated Feb. 25, 2015 for U.S. Appl. No. 13/275,495.
U.S. Office Action, Final, dated May 27, 2015 for U.S. Appl. No. 13/275,495.
U.S. Office Action, Non-Final, dated Jun. 6, 2016 for U.S. Appl. No. 13/275,495.
U.S. Office Action, Final, dated Dec. 21, 2016 for U.S. Appl. No. 13/275,495.
Office Action Non-Final dated Jan. 6, 2014 for U.S. Appl. No. 13/275,514.
U.S. Office Action, Non-Final, dated Sep. 9, 2014 for U.S. Appl. No. 13/275,514.
U.S. Office Action, Non-Final, dated May 21, 2015 for U.S. Appl. No. 13/275,514.
U.S. Office Action, Final, dated Sep. 11, 2015 for U.S. Appl. No. 13/275,514.
U.S. Office Action, Notice of Allowance, dated Nov. 25, 2015 for U.S. Appl. No. 13/275,514.
U.S. Office Action, Notice of Allowance, dated Mar. 2, 2016 for U.S. Appl. No. 13/275,514.
Office Action Non-Final dated May 17, 2013 for U.S. Appl. No. 13/275,547.
Office Action Final dated Feb. 28, 2014 for U.S. Appl. No. 13/275,547.
U.S. Office Action, Non-Final, dated Aug. 20, 2014 for U.S. Appl. No. 13/275,547.
U.S. Office Action, Final, dated Mar. 10, 2015 for U.S. Appl. No. 13/275,547.
U.S. Office Action, Non-Final, dated Aug. 28, 2015 for U.S. Appl. No. 13/275,547.
U.S. Office Action, Final, dated May 6, 2016 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
U.S. Office Action, Non-Final, dated Oct. 23, 2014 for U.S. Appl. No. 13/275,563.
U.S. Office Action, Non-Final, dated May 28, 2015 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/246,660.
U.S. Office Action, Restriction Requirement, dated Jul. 9, 2014 for U.S. Appl. No. 13/276,660.
U.S. Office Action, Notice of Allowance, dated Jun. 17, 2015 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Office Action Final dated Mar. 21, 2014 for U.S. Appl. No. 13/276,673.
U.S. Office Action, Non-Final, dated Aug. 14, 2014 for U.S. Appl. No. 13/276,673.
U.S. Office Action, Final, dated Mar. 13, 2015 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Notice of Allowance dated Nov. 12, 2013 for U.S. Appl. No. 13/276,687.
Notice of Allowance dated Jun. 2, 2014 for U.S. Appl. No. 13/276,687.
U.S. Office Action, Notice of Allowance, dated Sep. 12, 2014 for U.S. Appl. No. 13/276,687.
U.S. Office Action, Notice of Allowance, dated Dec. 23, 2014 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Office Action Final dated Sep. 27, 2013 for U.S. Appl. No. 13/276,707.
U.S. Office Action, Non-Final, dated Jan. 29, 2015 for U.S. Appl. No. 13/276,707.
U.S. Office Action, Non-Final, dated Jul. 16, 2015 for U.S. Appl. No. 13/276,707.
Restriction Requirement dated Feb. 6, 2013 for U.S. Appl. No. 13/276,725.
U.S. Office Action, Non-Final, dated Aug. 20, 2014 for U.S. Appl. No. 13/276,725.
U.S. Office Action, Notice of Allowance, dated Mar. 13, 2015 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Final dated Nov. 8, 2013 for U.S. Appl. No. 13/276,745.
Office Action Non-Final dated Feb. 28, 2014 for U.S. Appl. No. 13/276,745.
U.S. Office Action, Notice of Allowance, dated Oct. 7, 2014 for U.S. Appl. No. 13/276,745.
U.S. Office Action, Notice of Allowance, dated Dec. 19, 2014 for U.S. Appl. No. 13/276,745.
U.S. Office Action, Restriction Requirement, dated Sep. 24, 2014 for U.S. Appl. No. 13/277,328.
U.S. Office Action, Non-Final, dated Dec. 8, 2014 for U.S. Appl. No. 13/277,328.
U.S. Office Action, Final, dated Mar. 24, 2015 for U.S. Appl. No. 13/277,328.
U.S. Office Action, Notice of Allowance, dated Jun. 1, 2015 for U.S. Appl. No. 13/277,328.
Indian Office Action, Examination Report, dated Oct. 22, 2019 for Application No. 3968/DELNP/2013, 7 pgs.
Indian Office Action, Examination Report, dated Nov. 30, 2019 for Application No. 4013/DELNP/2013, 6pgs.
Indian Office Action, Examination Report, dated Jul. 12, 2019 for Application No. 3960/DELNP/2013, 8 pgs.
U.S. Appl. No. 16/549,798, filed Aug. 23, 2019, by Houser et al., entitled: "Surgical Instrument With Charging Station and Wireless Communication."

* cited by examiner

STERILE MEDICAL INSTRUMENT CHARGING DEVICE

This application is a continuation of U.S. patent application Ser. No. 15/212,423, entitled "Sterile Medical Instrument Charging Device," filed on Jul. 18, 2016, published as U.S. Pub. No. 2016/0329614 on Nov. 10, 2016, issued as U.S. Pat. No. 10,660,695 on May 26, 2020, which is a continuation of U.S. patent application Ser. No. 13/151,503, entitled "Sterile Medical Instrument Charging Device," filed on Jun. 2, 2011, issued as U.S. Pat. No. 9,597,143 on Mar. 21, 2017.

PRIORITY

U.S. patent application Ser. No. 13/151,503, filed on Jul. 2, 2011, issued as U.S. Pat. No. 9,597,143 on Mar. 21, 2017, claims priority to U.S. Provisional Application Ser. No. 61/410,603, filed Nov. 5, 2010, entitled "Energy-Based Surgical Instruments," the disclosure of which is incorporated by reference herein.

U.S. patent application Ser. No. 13/151,503, Jul. 2, 2011, issued as U.S. Pat. No. 9,597,143 on Mar. 21, 2017, also claims priority to U.S. Provisional Application Ser. No. 61/487,846, filed May 19, 2011, entitled "Energy-Based Surgical Instruments," the disclosure of which is incorporated by reference herein.

BACKGROUND

With the advancement of the electronics industry, many medical devices that rely on some form of electric power may be adapted to contain most, if not all, of the required components within the medical device. More specifically, some medical devices may be adapted to use an internal or attachable power source instead of requiring the device to be plugged into an external power source by a cable. Merely exemplary devices that may be adapted to include a portable power source are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,416,101 entitled "Motor-Driven Surgical Cutting and Fastening Instrument with Loading Force Feedback," issued Aug. 26, 2008, the disclosure of which is incorporated by reference herein; U.S. Pat. No. 7,738,971 entitled "Post-Sterilization Programming of Surgical Instruments," issued Jun. 15, 2010, the disclosure of which is incorporated by reference herein; U.S. Pub. No. 2006/0079874 entitled "Tissue Pad for Use with an Ultrasonic Surgical Instrument," published Apr. 13, 2006, now abandoned, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, now abandoned, the disclosure of which is incorporated by reference herein; U.S. Pub. No. 2008/0200940 entitled "Ultrasonic Device for Cutting and Coagulating," published Aug. 21, 2008, now abandoned, the disclosure of which is incorporated by reference herein; U.S. Pub. No. 2009/0209990 entitled "Motorized Surgical Cutting and Fastening Instrument Having Handle Based Power Source," published Aug. 20, 2009, (now U.S. Pat. No. 8,657,174, issued Feb. 25, 2014), the disclosure of which is incorporated by reference herein; and U.S. Pub. No. 2010/0069940 entitled "Ultrasonic Device for Fingertip Control," published Mar. 18, 2010, (now U.S. Pat. No. 9,023,071, issued May 5, 2015), the disclosure of which is incorporated by reference herein. Similarly, various ways in which medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein.

Electrically powered medical devices such as those referred to herein may require an internal or otherwise integral power source (e.g., a battery or battery pack, etc.) to be charged or recharged immediately before use, during use, or otherwise. In some settings (e.g., those where a charging device is re-used several times, etc.), it may be desirable to provide some degree of isolation between a charging device and the medical device to thereby reduce the likelihood that the charging device will contaminate the medical device and/or to reduce the likelihood that the medical device will contaminate the charging device. Similarly, it may be desirable to facilitate charging or recharging of the power source within relatively close proximity to the location at which the medical device will be used in a medical procedure (e.g., within an operating room, etc.). While several systems and methods have been made and used to charge or recharge power sources, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
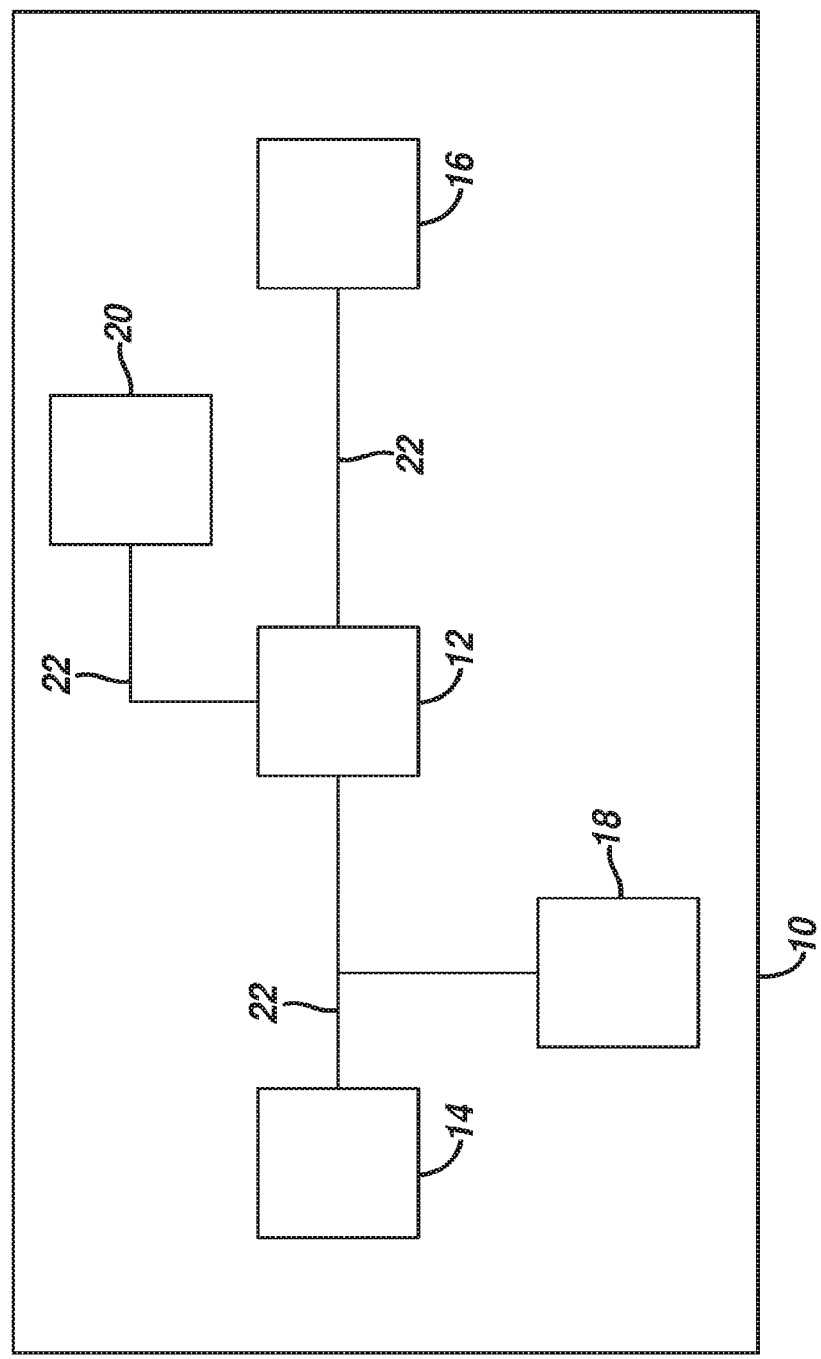
FIG. 1 depicts a schematic view of an exemplary medical device having an internal power source.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Medical Devices for Use with Insertable or Reclaimable Components

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
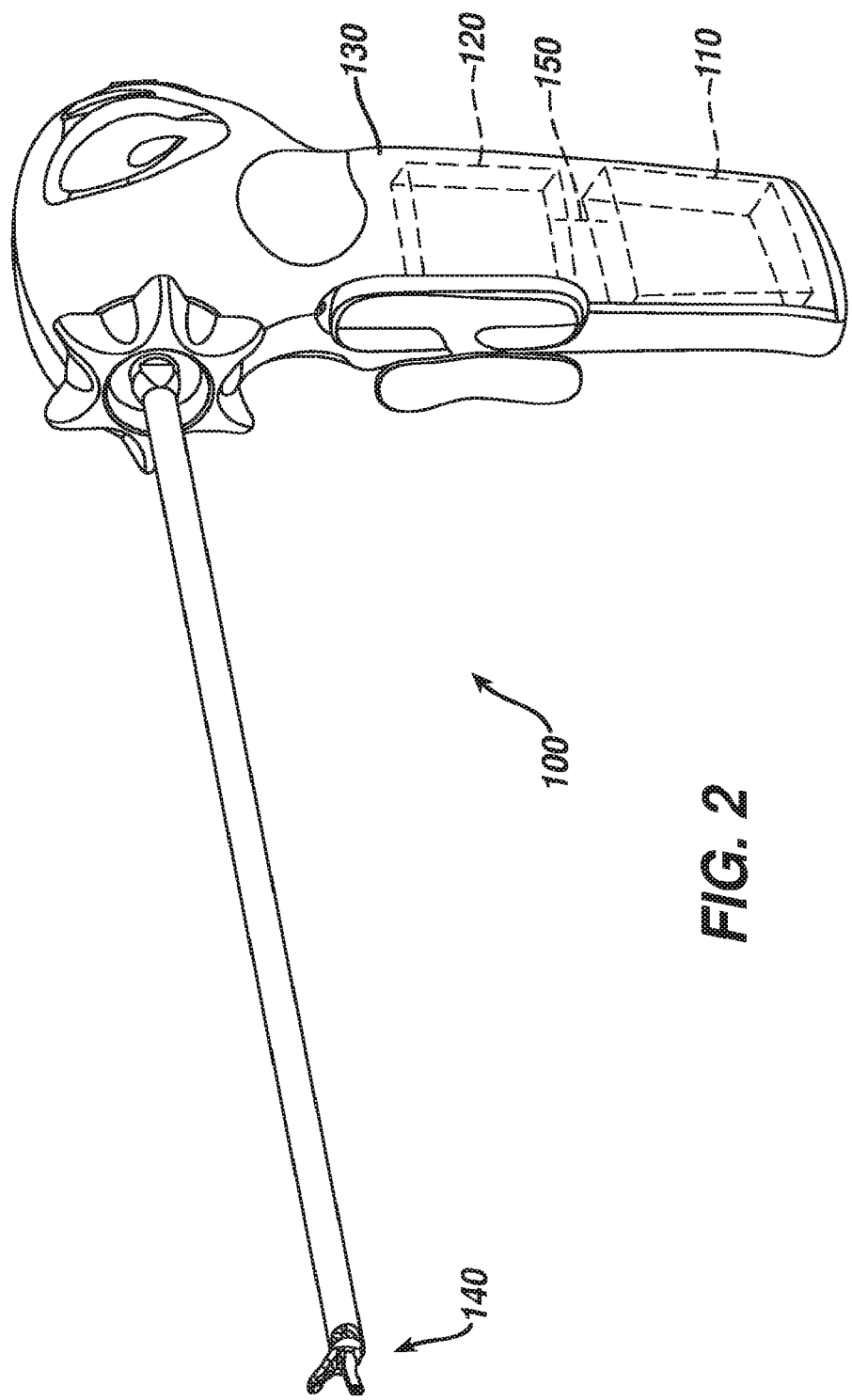
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from medical device (100) and decouple from control module (120) or electrical connection (150). As a result, power source (110) may be completely separated from medical device (100) in some versions. As is readily apparent, this may allow the power source (110) to be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein. While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. Nos. 6,500,176; 7,416,101; 7,738,971; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0209990 (now U.S. Pat. No. 8,657,174); U.S. Pub. No. 2010/0069940 (now U.S. Pat. No. 9,023,071); and/or U.S. Provisional Application Ser. No. 61/410,603.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which are filed on even date herewith and the disclosures of all of which are incorporated by reference herein: U.S. patent application Ser. No. 13/151,471, entitled "Medical Device Packaging with Charging Interface," published May 10, 2012 as U.S. Pub. No. 2012/0112690, issued as U.S. Pat. No. 9,000,720 on Apr. 7, 2015; U.S. patent application Ser. No. 13/151,481, entitled "Motor Driven Electrosurgical Device with Mechanical and Electrical Feedback," issued as U.S. Pat. No. 9,161,803 on Oct. 20, 2015; U.S. patent application Ser. No. 13/151,488, entitled "Packaging for Reclaimable Component of a Medical Device," published May 10, 2012 as U.S. Pub. No. 2012/0111591, now abandoned; U.S. patent application Ser. No. 13/151,498, entitled "Sterile Housing for Non-Sterile Medical Device Component," issued a U.S. Pat. No. 9,017,851 on Apr. 28, 2015; U.S. patent application Ser. No. 13/151,509, entitled "Medical Device Packaging with Window for Insertion of Reusable Component," issued as U.S. Pat. No. 9,089,338 on Jul. 28, 2015; U.S. patent application Ser. No. 13/151,512, entitled "Medical Device with Feature for Sterile Acceptance of Non-Sterile Reusable Component," issued as U.S. Pat. No. 9,072,523 on Jul. 7, 2015; and U.S. patent application Ser. No. 13/151,515, entitled "Sterile Package System for Medical Device," issued as U.S. Pat. No. 10,080,813 on Sep. 25, 2018. Various suitable ways in which teachings herein may be combined with teachings of the above-referenced patent applications, as well as various ways in which teachings of the above-referenced patent applications may be combined together with or without teachings herein, will be apparent to those of ordinary skill in the art.

Figure 3:
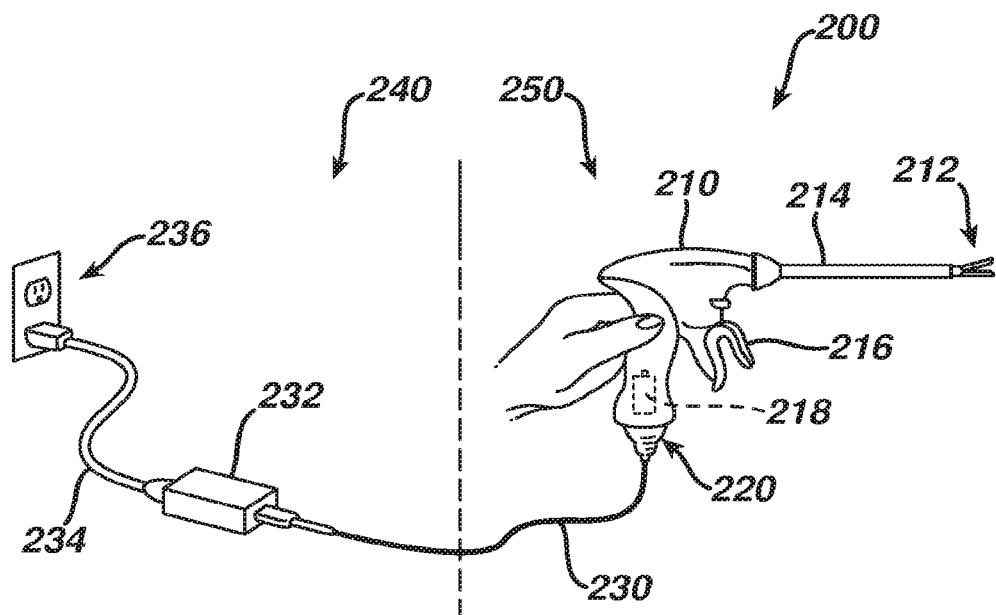
FIG. 3 depicts a perspective view of an exemplary medical device system including a cable and battery combination.

II. Exemplary Medical Device System Including Combined Integral Power Source and External Power Source FIG. 3 shows an exemplary medical device (200) that includes an integral power source (218) and that also relies on external power. Medical device (200) of this example includes a handpiece (210), an end effector (212) disposed at the distal end of a shaft (214), and a trigger (216). Integral power source (218) is included within the handpiece (210) and selectively activates end effector (212) in accordance with actuations of trigger (216). By way of example only, end effector (212) may comprise a harmonic blade, a pair of clamping jaws, and/or one or more electrosurgical elements. It should be understood that medical device (200) may be constructed and operable in accordance with medical device (10, 100) and/or in accordance with at least some of the teachings of any of the references cited herein. Various other kinds of devices to which the teachings of medical device (200) may be applied will be apparent to those of ordinary skill in the art in view of the teachings herein.

In the present example, integral power source (218) includes a single battery. In particular, integral power source (218) in this example provides enough power in a single charge to activate end effector (212) one or more times during a normal use of medical device (200) in a medical procedure. However, integral power source (218) in this example does not necessarily provide enough power to activate end effector (212) as many times as needed during a normal use of medical device (200) in a medical procedure without providing at least some degree of recharging of integral power source (218). To that end, a relatively thin charging wire (230) is coupled with handpiece (210) at coupling (220). Charging wire (230) is also coupled with an adapter (232), which is further coupled with a conventional power cable (234). Power cable (234) is plugged into a conventional wall outlet (236), though it should be understood that charging wire (230), adapter (232), and/or power cable (234) may alternatively be coupled with a piece of capital equipment and/or some other component.

Charging wire (230) is operable to deliver enough power to integral power source (218) to sufficiently charge integral power source (218) during a normal use of medical device (200) in a medical procedure. However, in the present example, charging wire (230) does not have sufficient thickness to provide all power needed to activate end effector (212) during normal use of medical device (200) in a medical procedure. Thus, charging wire (230) and integral power source (218) work in tandem—with integral power source (218) being the primary power source for end effector (212) and with charging wire (230) being used to recharge integral power source (218) (e.g., between selective activations of end effector (212), etc.).

Charging wire (230) of the present example is also substantially thinner than conventional power cable (234). It should be understood that this may provide greater mobility for medical device (200) due to reduced weight pulling on handpiece (210), particularly if adapter (232) and cable (234) rest on the floor. As is also shown in FIG. 3, power cable (234) and adapter (232) are located in a non-sterile field (240) while charging wire (230) and the rest of medical device (200) are located in a sterile field (250) in the present example. It should be understood that this may facilitate re-use of power cable (234) and adapter (232) in various medical procedures with various medical devices (200), without having to re-sterilize power cable (234) and adapter (232) for each re-use. Of course, it may still be desirable to sterilize charging wire (230) and the rest of medical device (200) before medical device (200) is used in a medical procedure, regardless of whether charging wire (230) and/or other parts of medical device (200) are re-used in subsequent medical procedures. In instances where charging wire (230) and medical device (200) are provided in a sterile kit before use, integral power source (218) may be provided with a partial charge in the kit.

In some versions, using a single battery for integral power source (218) may help reduce the overall cost and weight of medical device (200). In other words, using a larger integral power source (218) that is capable of activating end effector (212) enough times during normal use of medical device (200) without such a power source (218) having to be recharged might result in a more expensive and/or heavier medical device (200). Of course, integral power source (218) may comprise more than one battery or may even comprise some kind of power source other than a battery. Furthermore, integral power source (218) may be configured to hold enough charge sufficient to activate end effector (212) enough times during normal use of medical device (200) without such a power source (218) having to be recharged.

Figure 4:
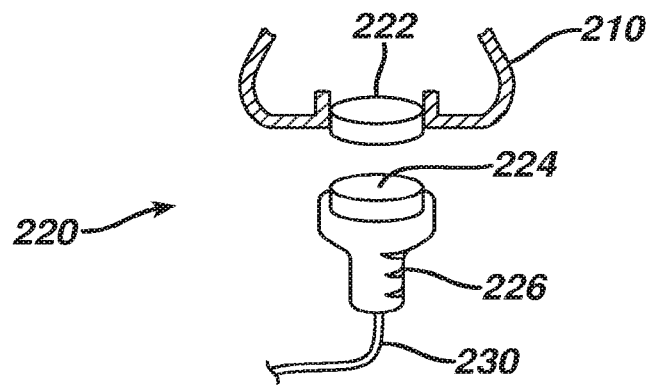
FIG. 4 depicts a partial cross-sectional view of a cable connector of the system of FIG. 3.
Figure 5:
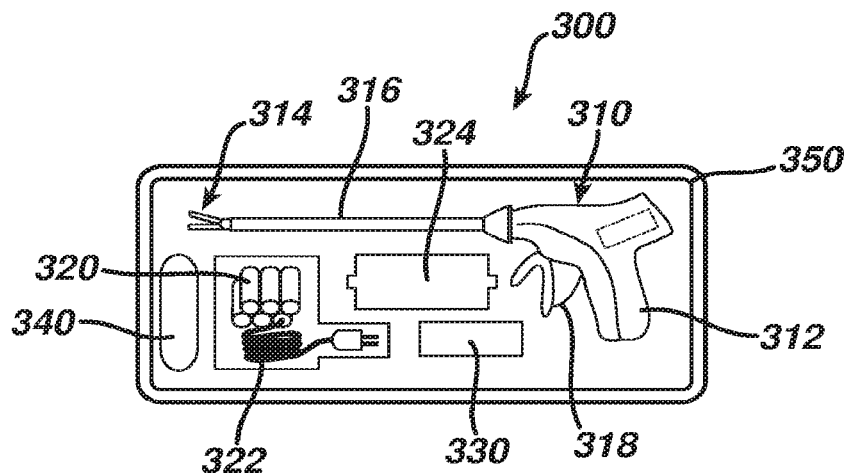
FIG. 5 depicts an exemplary medical device with components in a packaging system.

FIG. 4 shows coupling (220) of the present example in greater detail. As shown, coupling (220) a first magnet (222) integral with handpiece (210) and a second magnet (224) integral with a strain relief (226) on wire (230). In the present example, magnets (222, 224) provide relatively quick and easy coupling/decoupling of wire (230) and handpiece (210). In some versions, handpiece (210) and wire (230) also present complementary contacts, prongs and sockets, and/or other features to provide electrical communication from wire (230) to integral power source (218). Magnets (222, 224) may be located adjacent to such electrical communication features. Handpiece (210) and/or wire (230) may also include one or more bosses or other guide features configured to facilitate proper coupling of wire (230) with handpiece (210). It should also be understood that magnets (222, 224) are merely optional, and that a variety of other types of features may be used, including but not limited to latches, clamps, clips, friction fittings, etc.

In some instances, a surgeon may wish to decouple wire (230) from handpiece (210) to provide greater mobility or positioning of medical device (200). In such instances, wire (230) may be readily re-coupled with handpiece (210) at coupling (220), even in the operating room, to provide any additional charge that may be needed for integral power source (218) after one or more activations of end effector (212). Furthermore, handpiece (210) or some other component of medical device (200) may include a charge indicator, providing a visual and/or audio indication of the charge state of power source (218), thereby alerting the surgeon to when power source (218) needs to be recharged. Still other suitable components, features, configurations, and operabilities of medical device (200) will be apparent to those of ordinary skill in the art in view of the teachings herein.

III. Exemplary Medical Device Kit Including Electronic Component Charging and Reclamation Features FIGS. 5-9 show an exemplary kit (300) and its various components, including a medical device (310), batteries (320), a control module (330) (e.g., printed circuit board, generator board, etc.), and a reclamation bag (340), all of which are positioned in respective compartments of packaging (350). Packaging (350) of the present example comprises a sterile blister pack, though it should be understood that packaging (350) may take any other suitable form. In some versions, packaging (350) is constructed in accordance with the teachings of U.S. patent application Ser. No. 13/151,515, entitled "Sterile Package System for Medical Device," filed Jun. 2, 2011, issued as U.S. Pat. No. 10,080,813 on Sep. 25, 2018, the disclosure of which is incorporated by reference herein. For instance, such a form of packaging (350) may facilitate sterilization and sealing of medical device (310) separate from sterilization and sealing of batteries (320) and control module (330). Various other suitable ways in which packaging (350) may be configured will be apparent to those of ordinary skill in the art in view of the teachings herein.

Figure 7:
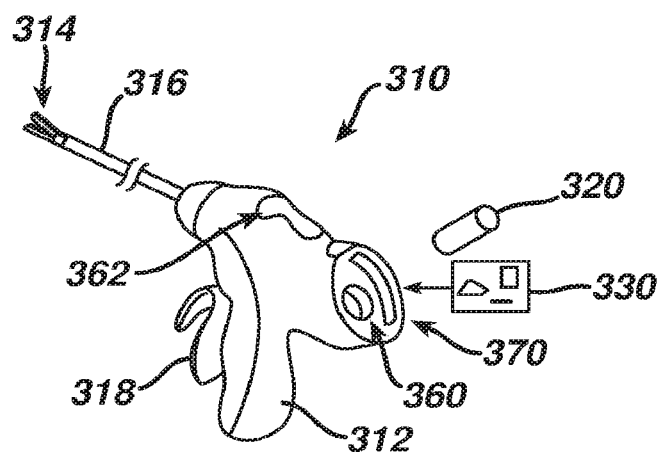
FIG. 7 depicts a perspective view of the medical device of FIG. 5 with a battery and control module positioned for insertion in the medical device.

Medical device (310) of the present example includes a handpiece (312), an end effector (314) disposed at the distal end of a shaft (316), and a trigger (318). As shown in FIG. 7, handpiece (312) includes a first slot (360) configured to receive battery (320) and a second slot (370) configured to receive control module (330). Such slots (360, 370) may include latching features configured to selectively retain battery (320) and control module (330) in handpiece (312) after insertion. Slots (360, 370) may also include leads sufficient to establish electrical communication with inserted battery (320) and control module (330). By way of example only, either slot (360, 370) may be configured in accordance with the teachings of U.S. patent application Ser. No. 13/151,512, entitled "Medical Device with Feature for Sterile Acceptance of Non-Sterile Reusable Component," filed Jun. 2, 2011, issued as U.S. Pat. No. 9,072,523 on Jul. 7, 2015, the disclosure of which is incorporated by reference herein. Other suitable configurations for slots (360, 370) will be apparent to those of ordinary skill in the art in view of the teachings herein. In some versions, a charged battery (320) is preloaded in handpiece (312), such that medical device (310) is immediately ready for use upon removal from packaging (350). In some such instances, remaining batteries (320) in packaging (350) are simply relied on for backup in the event that the preloaded battery (320) loses sufficient charge.

Once coupled with handpiece (312), battery (320) and control module (330) cooperate to selectively activate end effector (314) in accordance with actuations of trigger (318). As also shown in FIG. 7, handpiece (312) of the present example also includes a battery life indicator (362), which is operable to indicate how much charge is left in battery (320). As with other components described herein, battery life indicator (362) is merely optional. If the charge level of a battery (320) gets too low during a medical procedure, the user may simply eject battery (320) as described below and use another, fully charged battery (320) from packaging (350). In some instances, having several batteries (320) on hand in packaging (350) may facilitate use of relatively small batteries (320), which may in turn reduce the overall weight of medical device (310) during use of medical device (310) in a medical procedure. Extra batteries (320) may continue to be charged in packaging (350) during the medical procedure.

By way of example only, end effector (314) may comprise a harmonic blade, a pair of clamping jaws, and/or one or more electrosurgical elements. It should be understood that medical device (310) may be constructed and operable in accordance with medical device (10, 100) and/or in accordance with at least some of the teachings of any of the references cited herein. Various other kinds of devices to which the teachings of medical device (310) may be applied will be apparent to those of ordinary skill in the art in view of the teachings herein.

Figure 6:
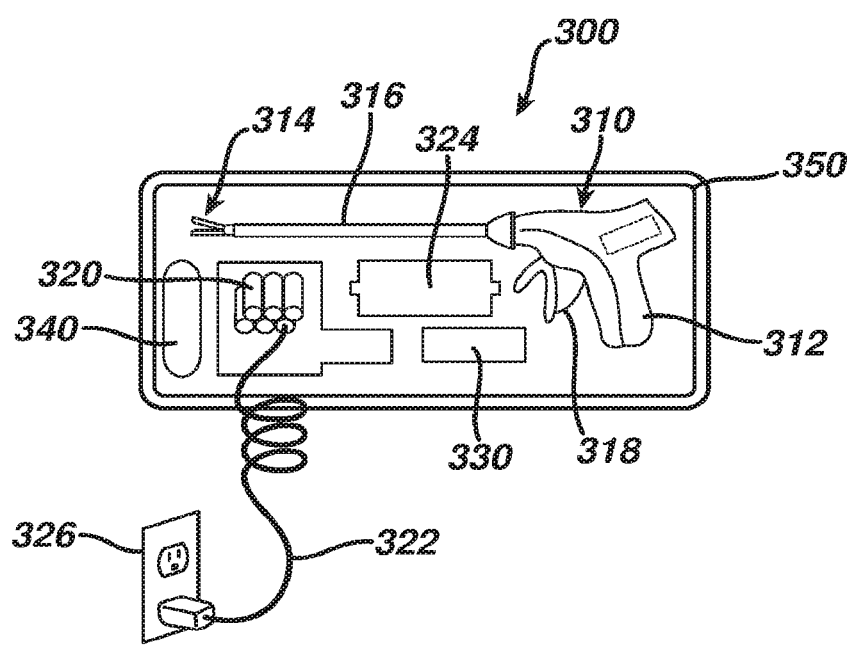
FIG. 6 depicts the system of FIG. 5 with battery components being charged in the packaging.

As best seen in FIG. 6, kit (300) also includes a power cord (322) coupled with batteries (320). In the present example, power cord (322) is coupled with batteries (320) via a charger (324) that is integral with packaging (350) (e.g., disposed within a recess formed by packaging (350), etc.). When plugged into a conventional wall outlet (326) (or some other power source), power cord (322) is operable to charge batteries (320). In some versions, kit (300) is shipped and stored with batteries (320) having only a partial charge, such that batteries (320) need to be charged before medical device (310) is used in a medical procedure. In other words, in an exemplary use, a user may initially receive kit (300) in the form shown in FIG. 5, which may include a peelable film cover, lid, or other removable feature. Right before medical device (310) is to be used in a medical procedure, the user may place kit (300) on a mayo stand in the operating room (or place kit (300) elsewhere), remove the film cover, lid, or other removable feature, and then plug power cord (322) into wall outlet (326) as shown in FIG. 6. Charger (324), packaging (350), and/or batteries (320) may include visual and/or audio indicators configured to convey the charge state of batteries (320) to the user. Once batteries (320) are sufficiently charged, the user may then insert battery (320) and control module (330) into respective slots (360, 370) of handpiece (312), as shown in FIG. 7. Medical device (310) is then ready to be used in a medical procedure.

Figure 8:
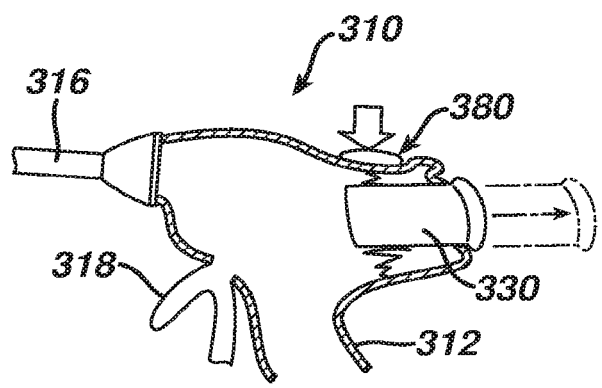
FIG. 8 depicts a partial cross-sectional view of the medical device of FIG. 5 ejecting the control module.

Handpiece (312) of the present example also includes a component ejection feature (380), which includes a button and a spring-loaded release mechanism. As shown in FIG. 8, component ejection feature (380) is operable to eject control module (330) and battery (320) from handpiece (312). In some versions, a single component ejection feature (380) simultaneously ejects both battery (320) and control module (330). In some other versions, separate component ejection features (380) are provided for independent ejection of battery (320) and control module (330). It should be understood that it may be desirable in some instances to eject battery (320) and/or control module (330) from medical device (310), such as after the medical procedure is complete. For instance, it may be desirable in some instances to dispose of battery (320) and/or control module (330) separate from disposal of other components of medical device (310), such as to avoid environmental concerns.

Figure 9:
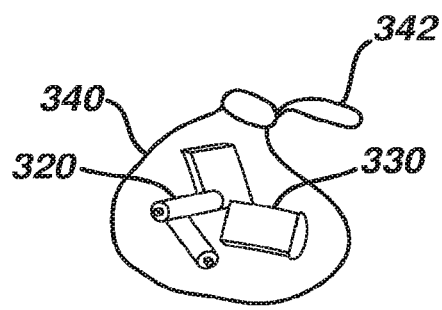
FIG. 9 depicts a perspective view of a reclamation bag of the system of FIG. 5 holding electronic components of the system of FIG. 5.

As another merely illustrative example, it may be desirable in some instances to separately collect batteries (320) and/or control module (330) for reclamation (e.g., cleaning and re-sterilization, etc.) and re-use. For instance, this may be desirable where battery (320) and/or control module (330) are relatively high cost items; and/or to again avoid environmental concerns that might be associated with simple disposal of battery (320) and/or control module (330). As shown in FIG. 9, reclamation bag (340) may be used to collect used batteries (320), control module (330), and/or other components (e.g., charger (324), etc.). Filled reclamation bag (340) may then be sent off to reclaim, salvage, or otherwise further process the components contained therein, with the remainder of kit (300) being discarded or otherwise disposed of. In the present example, reclamation bag (340) includes a drawstring (342), though it should be understood that any other suitable type of closure feature may be used.

In some versions, control module (330) is not removable from medical device (310), such that only battery (320) is removable from medical device (310). Similarly, in some versions control module (330) is removable from medical device (310) and either battery (320) is non-removable or medical device (310) receives power from some other source. It should also be understood that charger (324) or some other feature of kit (300) may be configured to safely discharge batteries (320) before batteries (320) are disposed of or sent off for reclamation/processing in reclamation bag (340). Still other suitable components, features, configurations, and operabilities of kit (300) will be apparent to those of ordinary skill in the art in view of the teachings herein.

IV. Exemplary Medical Device Conductive Charging Stations

As noted above, in medical devices having internal power sources such as batteries, etc., it may be necessary to charge or recharge such internal power sources before and/or during use of the medical device in a medical procedure. In some instances, this may require physically coupling (e.g., via contact) a component of the medical device with a component of a docking station or other type of charging device. In some settings, such physical contact may present concerns as to sterility. In particular, such as situations where the docking station or other charging device is re-used, it may be desirable in some instances to provide ready re-use of such a docking station or other charging device without necessarily having to fully re-sterilize the docking station or other charging device between uses. Thus, in some situations where the docking station or other charging device is not sterile, it may be desirable to prevent such non-sterility from contaminating a sterile medical device when some degree of contact is required between the docking station or other charging device and the medical device in order to charge/recharge the medical device. The following examples present ways in which a non-sterile charging device may be used to charge a sterile medical device without compromising the sterility of the medical device despite some degree of contact with the medical device. Further examples and variations will be apparent to those of ordinary skill in the art in view of the teachings herein.

A. Exemplary Charging Station with Sterile Barrier

Figure 10:
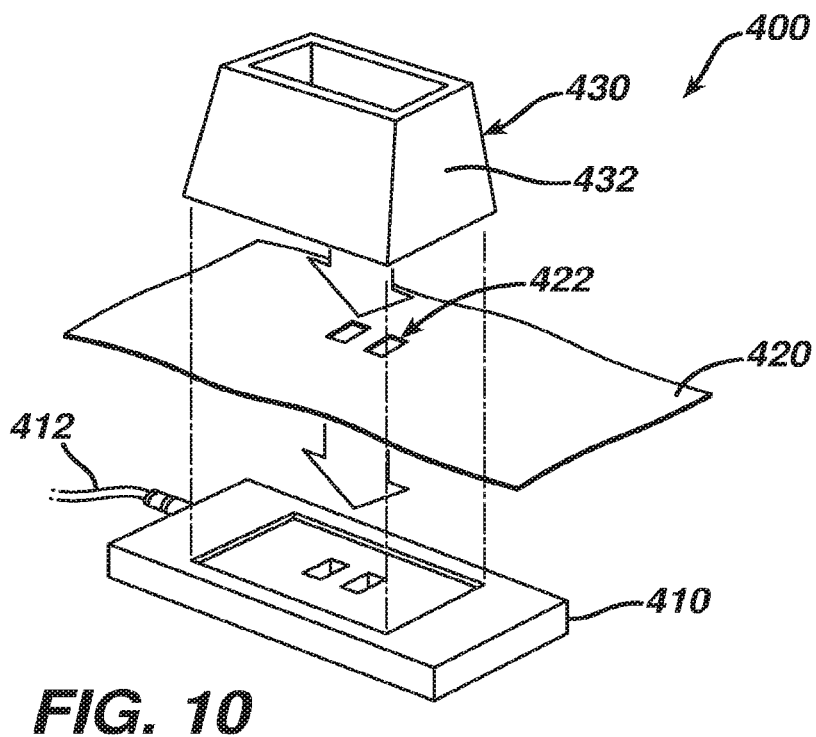
FIG. 10 depicts an exploded view of exemplary medical device recharging assembly.
Figure 11:
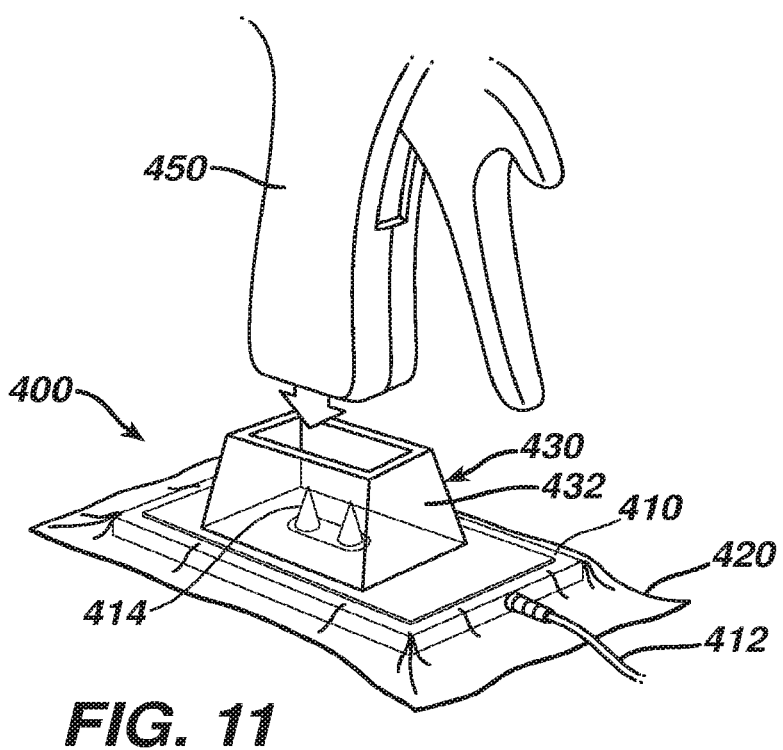
FIG. 11 depicts a perspective view of a medical device positioned over the recharging assembly of FIG. 10.
Figure 12:
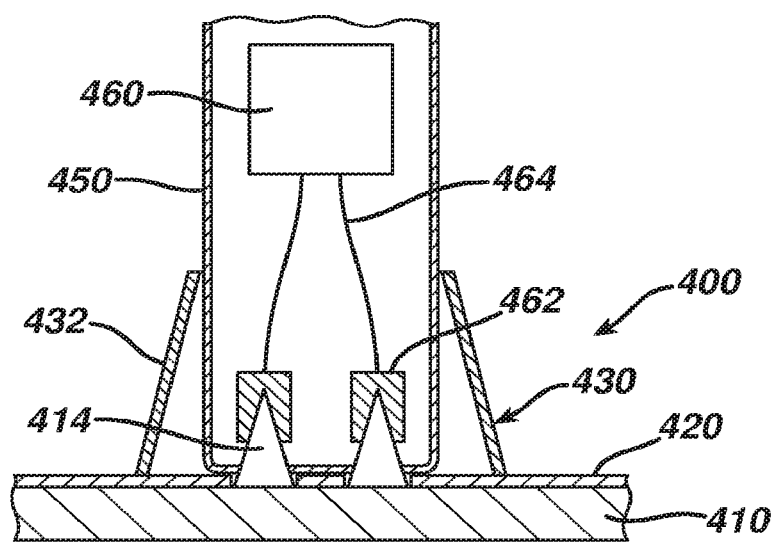
FIG. 12 depicts a partial cross-sectional view of the medical device of FIG. 11 coupled with the recharging assembly of FIG. 10.

FIGS. 10-12 show an exemplary charging station (400) that includes a base (410), a film (420), and a collar (430). Charging station (400) is shown as coupling with a handpiece (450) of a medical device. As shown in FIG. 12, handpiece (450) includes an integral power source (460) and a pair of contacts (462) that are coupled with power source (460) via wires (464). Power source (460) may comprise one or more batteries and/or various other components. Contacts (462) are recessed within handpiece (450) in this example. In some versions, contacts (462) define or are provided in respective sockets. It should be understood that the medical device having handpiece (450) may be constructed and operable in accordance with medical device (10, 100) and/or in accordance with at least some of the teachings of any of the references cited herein. Various other types of devices that may include handpiece (450) will be apparent to those of ordinary skill in the art in view of the teachings herein.

Base (410) includes a power cord (412) that is configured to plug into a conventional wall outlet or a piece of capital equipment. A pair of spike contacts (414) protrude upwardly from base (410). While spike contacts (414) have a sharp conical shape in the present example, it should be understood that contacts (414) may have any other suitable shape. Contacts (462) of handpiece (450) are configured to receive spike contacts (414) when handpiece is coupled with charging station (400), such that spike contacts (414) are operable to charge power source (460). Collar (430) is configured to insertingly receive a lower portion of handpiece (450) and is configured to provide structural support to handpiece (450). In particular, collar (430) has angled sidewalls (432) providing a tapered configuration, which helps prevent handpiece (450) and collar (430) from tipping over. While contacts (414) are shown protruding upwardly from base (410), it should be understood that the contacts (414) could alternatively reside and point downwardly from within handpiece (450) and make contact with contacts of base (410).

Film (420) comprises a sterile sheet of plastic film, and is configured to provide a sterile barrier between the exterior of sterile handpiece (450) and non-sterile base (410). In particular, film (420) is interposed between handpiece (450) and base (410). In the present example, collar (430) is also sterile, and is also positioned above film (420). It should be understood, however, that film (420) may optionally be draped over collar (430), and that film (420) may deform when handpiece (450) is inserted in collar (430), such that film (420) may serve as a sterile barrier between the sterile exterior of handpiece (450) and a non-sterile collar (430). As best seen in FIG. 10, film (420) of the present example includes a pair of openings (422) associated with spike contacts (414). In particular, openings (422) are sized and configured to permit passage of spike contacts (414) therethrough. In some other versions, openings (422) are eliminated, and spike contacts (414) pierce and poke through film (420) when handpiece (450) is pressed onto base (410) through collar (430).

In some versions, spike contacts (414) are selectively retractable within base (410). For instance, spike contacts (414) may be retracted in base (410) as charging station (400) is being prepared for use, as shown in FIG. 10. Base (410) may include an actuating mechanism (not shown) that is operable to deploy spike contacts (414) at an appropriate time. Such a mechanism may employ springs, solenoids, and/or various other types of components to deploy spike contacts (414). By way of example only, base (410) may include a button, switch, slider, or other feature operable to selectively activate such an actuation mechanism. As another merely illustrative example, base (410) may include a feature that is responsive to placement of collar (430) and/or handpiece (450) against base (410), such that spike contacts (414) deploy upon placement of collar (430) and/or handpiece (450) against base (410).

In some other versions, spike contacts (414) are integral features of collar (430) instead of being integral features of base (410). For instance, base (410) may present a pair of contacts that mate with complementary contacts on the underside of collar (430), through openings (422) in film (420). Such contacts on the underside of collar (430) may be in communication with spike contacts (414). Still other suitable components, features, configurations, and operabilities of charging station (400) will be apparent to those of ordinary skill in the art in view of the teachings herein.

B. Exemplary Charging Station with Breakaway Prongs

Figure 13A:
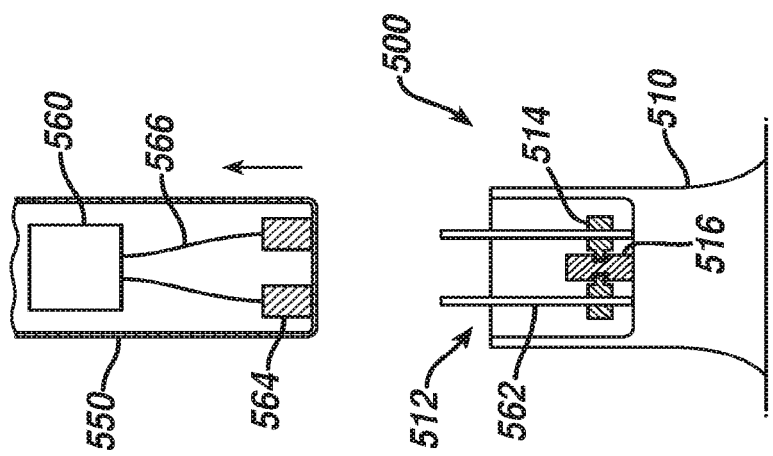
FIG. 13A depicts a partial cross-sectional view of another exemplary medical device recharging assembly, with a medical device positioned over the recharging assembly.
Figure 13B:
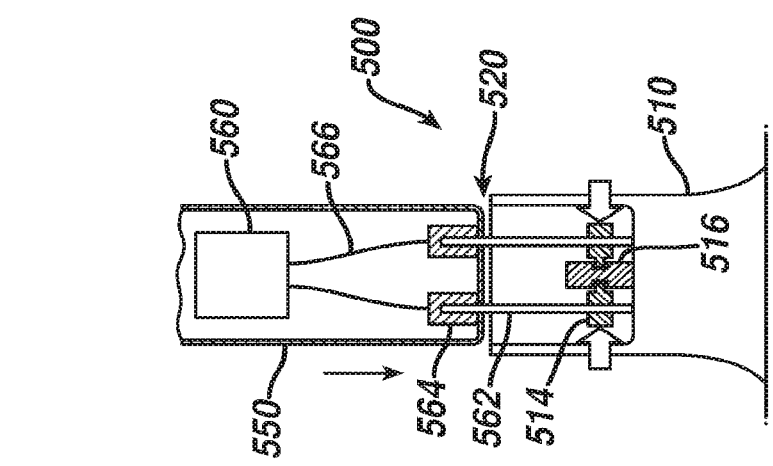
FIG. 13B depicts a partial cross-sectional view of the recharging assembly of FIG. 13A, with the medical device being coupled with the recharging assembly.
Figure 13C:
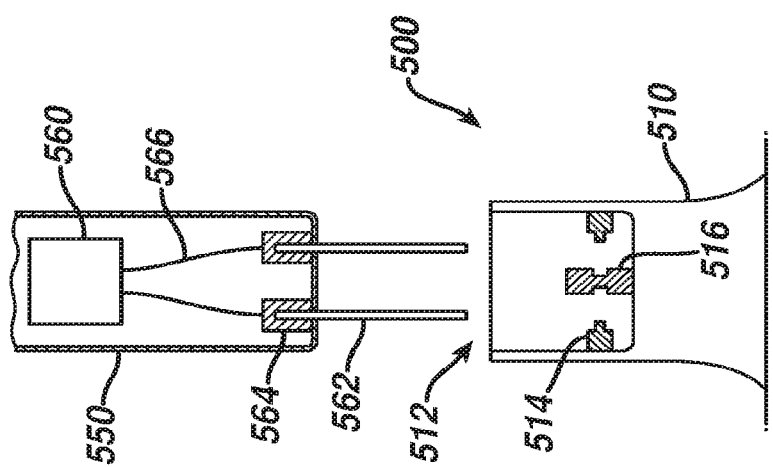
FIG. 13C depicts a partial cross-sectional view of the recharging assembly of FIG. 13A, with the medical device removed and leaving behind recharging prongs.

FIGS. 13A-13C show another exemplary charging station (500) that includes a base (510) having a recess (512) and movable retention pins (514). Recess (512) is sized and shaped to receive a lower portion of a handpiece (550) of a medical device. Handpiece (550) of this example includes an integral power source (560) and a pair of protruding prongs (562) that are removably received in sockets (564) of handpiece (550). For instance, sockets (564) may include conductive leaf spring features and/or other features that substantially hold prongs (562) in sockets (564) yet release prongs (562) from sockets (564) when prongs (562) are pulled from sockets (564) with sufficient force. Sockets (564) are further coupled with power source (560) via wires (566). Power source (560) may comprise one or more batteries and/or various other components. It should be understood that the medical device having handpiece (550) may be constructed and operable in accordance with medical device (10, 100) and/or in accordance with at least some of the teachings of any of the references cited herein. Various other types of devices that may include handpiece (550) will be apparent to those of ordinary skill in the art in view of the teachings herein.

Base (510) of the present example includes a cable (not shown) that is configured to plug into a conventional wall outlet or piece of capital equipment, etc., to deliver a charge to power source (560) as described in greater detail below. Retention pins (514) are configured to move toward a central member (516) within recess (512) when prongs (562) are sufficiently positioned within recess (512). By way of example only, base (510) may include a spring-loaded trip mechanism that is responsive to insertion of prongs (562) in recess, and such a trip mechanism may cause pins (514) to move toward central member (516) as shown in FIG. 13B. Such a trip mechanism may include one or more springs or other resilient members, levers, rockers, cams, etc. As can be seen in FIGS. 13B-13C, pins (514) are configured to trap prongs (562), such as by passing through corresponding openings (not shown) formed in prongs (562). In addition, pins (514) are conductive and are configured to deliver a charge to prongs (562) to thereby charge power source (560). It should therefore be understood that, in some versions, central member (516) is made of a non-conductive material, such that pins (514) will not short out when they both contact central member (516).

As can also be seen in FIG. 13B, the relative lengths of prongs (562) and recess (512) are selected such that handpiece (550) does not have to contact base (510) during charging. In particular, a gap (520) is presented between base (510) and handpiece (550). Thus, in the present example, charging station (500) may be non-sterilized and yet still not contaminate sterile handpiece (550) during charging of power source (560). In some other versions, the interior of recess (512) and at least a top portion of base (510) are sterilized to further avoid the risk of inadvertently contaminating sterile handpiece (550). It should also be understood that prongs (562) and recess (512) may have any other suitable relative lengths, such that gap (520) is eliminated and such that part of handpiece (550) is also disposed in recess (512) during charging of power source (560).

In an exemplary use, a user initially positions handpiece (550) over base (510) as shown in FIG. 13A. The user then urges handpiece (550) downwardly, such that prongs (562) are disposed in recess, and such that pins (514) move toward central member (516) to capture and contact prongs (562) as shown in FIG. 13B. Handpiece (550) remains in this position during charging of power source (560). The charge level of power source (560) may be monitored by a charge indicator on handpiece (550), on base (510), or elsewhere. Once power source (560) is sufficiently charged, handpiece (550) is pulled upwardly, leaving prongs (562) in base (510) as shown in FIG. 13C. In some versions, base (510) is weighted or otherwise secured to the surface on which it rests in order to provide sufficient resistance to friction encountered by prongs (562) in sockets (564), such that base (510) is not lifted away with handpiece (550) by prongs (562).

In some versions, handpiece (550) includes a door, cap, or other feature that is operable to close off sockets (564) when prongs (562) are pulled free from sockets (564), thereby effectively sealing off the bottom of handpiece (550). Such a feature may be manually operated after handpiece (550) is pulled away from base (510). Alternatively, a mechanism may automatically case such a feature to be released to close off sockets (564) when prongs (562) are pulled free from sockets (564). Various suitable ways in which such a feature may be provided will be apparent to those of ordinary skill in the art in view of the teachings herein. Similarly, various other suitable components, features, configurations, and operabilities of charging station (500) and handpiece (550) will be apparent to those of ordinary skill in the art in view of the teachings herein.

V. Exemplary Medical Device Inductive Charging Stations

The examples described above with reference to FIGS. 10-13C relate to conductive charging, where charging of a power source is provided through direct contact between conductive materials. An alternative form of charging includes the use of inductive coupling. In particular, energy is exchanged from one inductive coil to another inductive coil via an electromagnetic field, such that the coils together form a transformer, without the coils coming into physical contact with each other. In the context of medical devices, inductive charging may still present concerns as to sterility, though such concerns may be addressed differently in the context of inductive charging than they would be addressed in the context of conductive charging. As described in greater detail below, a non-sterile inductive charging station may be used to charge a power source in a sterile medical device without compromising the sterility of the medical device. While several such examples will be discussed in greater detail below, other examples and variations will be apparent to those of ordinary skill in the art in view of the teachings herein.

A. Exemplary Charging Pad with Wireless Communication of Charge State

Figure 14:
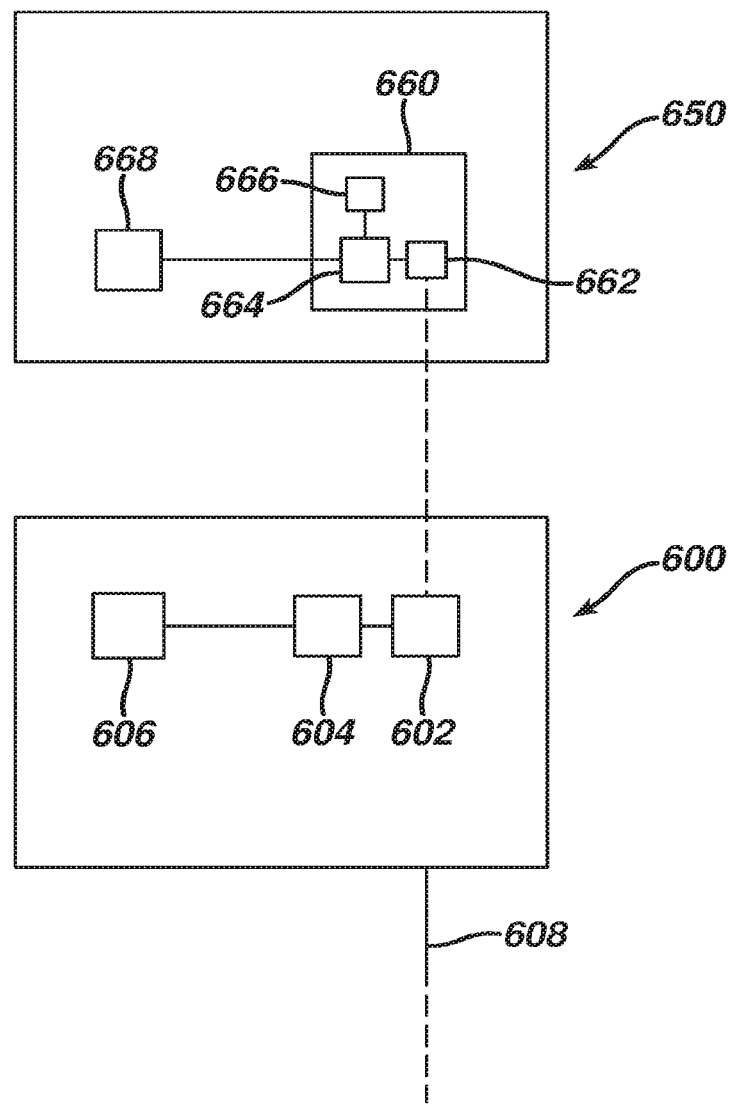
FIG. 14 depicts a schematic diagram of an exemplary wireless recharging system with wireless data communication.
Figure 15:
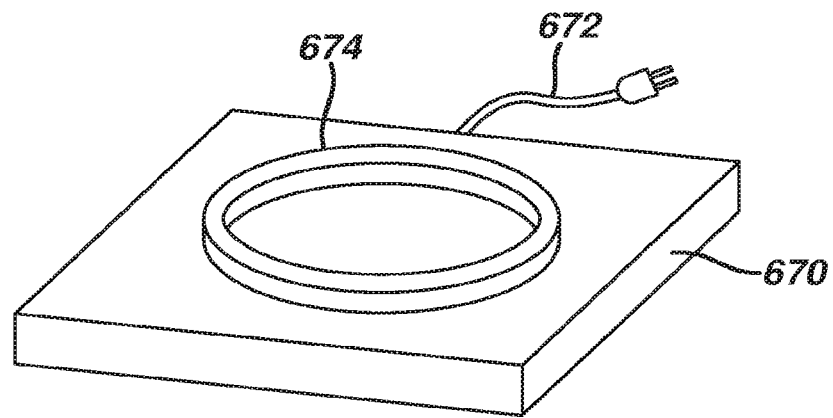
FIG. 15 depicts a perspective view of an exemplary version of a charging station provided in accordance with the system of FIG. 14.
Figure 16:
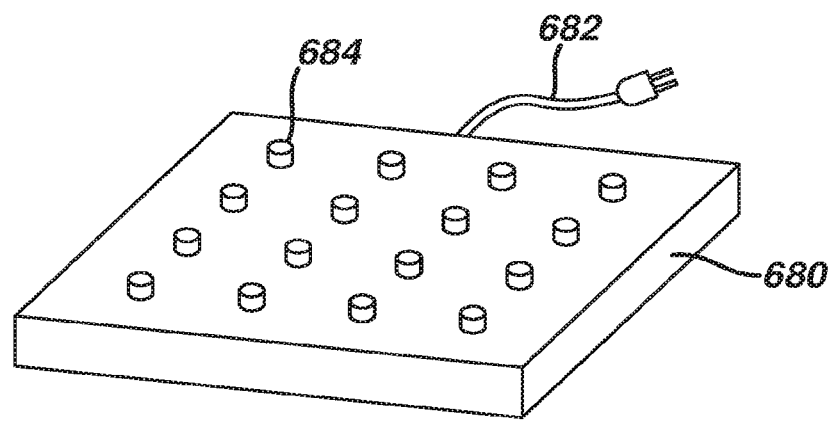
FIG. 16 depicts a perspective view of another exemplary version of a charging station provided in accordance with the system of FIG. 14.

FIGS. 14-16 depict examples of inductive charging pads that may be used to provide inductive charging and wireless communication of charge state. In particular, FIG. 14 schematically depicts a charging pad (600) and a medical device (650). Charging pad (600) of this example includes a primary inductive coil (602), a control module (604), a charge indicator (606), and a power cable (608). Power cable (608) is configured to plug into a conventional wall outlet or piece of capital equipment, etc., and thereby provide power to inductive coil (602). In addition to regulating the power transmitted via inductive coil (602), control module (604) is configured to superimpose data on the waveform transmitted by inductive coil (602), and is further configured to process data received by inductive coil (602), as will be described in greater detail below. In other words, control module (604) is configured to provide bi-directional data communication through inductive coil (602).

Medical device (650) of this example includes an integral power source (660), which includes a secondary inductive coil (662), a control module (664), and at least one battery (666). As with other control modules referred to herein, control module (664) may include a variety of components, including but not limited to a printed circuit board, a microprocessor, a memory device, etc. Various suitable components, features, and configurations for the various control modules referred to herein will be apparent to those of ordinary skill in the art in view of the teachings herein. Medical device (650) also includes a charge indicator (656) in this example, though it should be understood that in other versions either or both of charge indicators (606, 656) may be omitted. It should also be understood that medical device (650) may be constructed and operable in accordance with medical device (10, 100) and/or in accordance with at least some of the teachings of any of the references cited herein. For instance, medical device (650) may include an ultrasonic or electrosurgical end effector (not shown) that is selectively activated by power source (660). Various other types of forms that medical device (650) may take will be apparent to those of ordinary skill in the art in view of the teachings herein.

With power cable (608) plugged in, and when medical device (650) is brought within sufficient proximity of charging pad (600), coils (602, 662) inductively couple, thereby forming a transformer and allowing the wireless transfer of energy from coil (602) to coil (662), thereby charging battery (666) through induction of a current in coil (662). Control module (664) is operable to monitor the charge level of battery (666) in real time. Control module (664) is further operable to drive charge indicator (656) to indicate the charge level of battery (666) (e.g., visually and/or audibly) in real time. In addition, control module (664) is operable to communicate the charge level of battery (666) back to control module (664) via coils (662, 602). For instance, control module (664) may superimpose a data carrier on the charging waveform through modulation, allowing such data to be communicated form coil (662) to coil (602). Control module (604) may receive such data via coil (602) and react to it in various ways. For instance, control module (604) may drive charge indicator (606) to indicate the charge level of battery (666) (e.g., visually and/or audibly) in real time. In addition, control module (604) may adjust the charging current provided through coils (602, 662), based at least in part on the charge level of battery (666). Control modules (604, 664) may thus together provide a feedback loop, allowing the charging profile of battery (666) (e.g., frequency and/or other parameters) to be optimized in real time for whichever battery (666) is coupled with charging pad (600). Various suitable ways in which such communication between control modules (602, 664) and corresponding real time adjustments may be provided will be apparent to those of ordinary skill in the art in view of the teachings herein.

In some versions, the electronics in charging pad (600) may be encapsulated in a potting compound and/or be otherwise encapsulated. Such encapsulation may enable charging pad (600) to be sterilized using steam and/or other sterilization techniques that might otherwise not be available without damaging charging pad (600). Of course, charging pad (600) may be sterilized using a variety of other techniques, including but not limited to electron beam sterilization.

In some settings, it may be desirable to maximize the interface area of an inductive charging pad to maximize the amount of current that may be transferred to a battery pack or other type of power source. To that end, FIG. 15 shows an exemplary charging pad (670) that includes a power cord (672) and a relatively large primary coil (674). Primary coil (674) has a diameter spanning across almost the entire length and width of charging pad (670). Primary coil (674) may inductively couple with a similarly sized secondary coil in a medical device (not shown) to provide optimized inductive charging to a battery within the medical device. FIG. 16 shows an exemplary charging pad (680) that includes a power cord (682) and a plurality of smaller primary coils (684). While primary coils (684) are relatively small in this example, they are provided in an array that spans across almost the entire length and width of charging pad (690). Primary coils (684) may inductively couple with similarly sized and arranged secondary coils in a medical device (not shown) to provide optimized inductive charging to a battery or batteries within the medical device. It should also be understood that charging pad (690) may accommodate various different medical devices having inductive charging interfaces of various sizes (e.g., such that not all primary coils (684) are necessarily used every time). Still other suitable components, features, configurations, and operabilities of charging pad (600, 670, 680) and medical device (650) will be apparent to those of ordinary skill in the art in view of the teachings herein. It should also be understood that any charging pad or charging device referred herein may include the communication capabilities discussed above with respect to charging pad (600), if desired.

B. Exemplary Charging Pad on Stand with Sterile Drape

Figure 17:
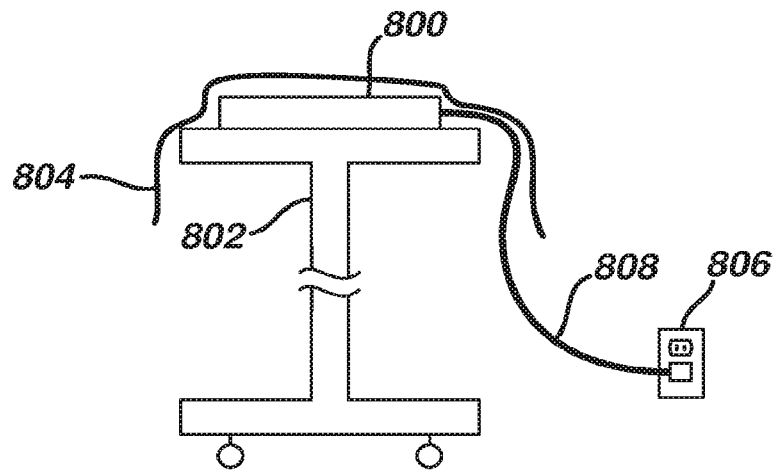
FIG. 17 depicts a schematic view of an exemplary inductive charging pad system.

As noted above, an inductive charging pad may be sterilized using steam, electron beam sterilization, and/or using other sterilization techniques. It should also be understood, however, that an inductive charging pad may still be used, even in an operating room, without the charging pad necessarily being sterilized, and without the non-sterile charging pad compromising the sterility of the medical device that it charges. For instance, as shown in FIG. 17, an inductive charging pad (800) may be placed on a mayo stand (802) (or elsewhere) in an operating room, and a sterile drape (804) may be placed over charging pad (800) to act as a sterile barrier. Thus, during an operation, and with charging pad (800) plugged into a conventional wall outlet (806) via a cable (808), sterile battery packs (not shown) that are capable of being inductively charged may simply be placed directly on sterile drape (804) over charging pad (800). For instance, such battery packs may have integral inductive charging coils that establish communication with one or more complementary coils in charging pad (800). Such battery packs may thus be charged by charging pad (800) through sterile drape (804), and sterile drape (804) may help maintain the sterility of the battery packs by preventing contamination from non-sterile charging pad (800). Sterile drape (804) may comprise any suitable material and construction, including but not limited to a plastic film, a suitable fabric, etc.

C. Exemplary Charging Peg on Stand with Sterile Drape

Figure 18:
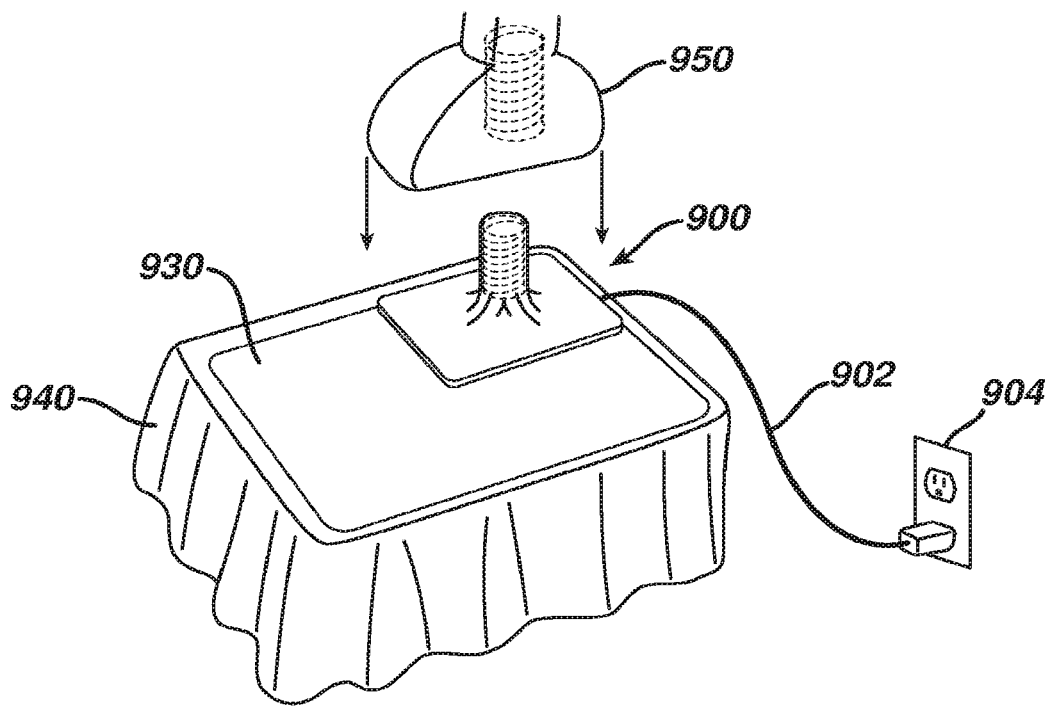
FIG. 18 depicts a perspective view of an exemplary inductive charging peg system.
Figure 19:
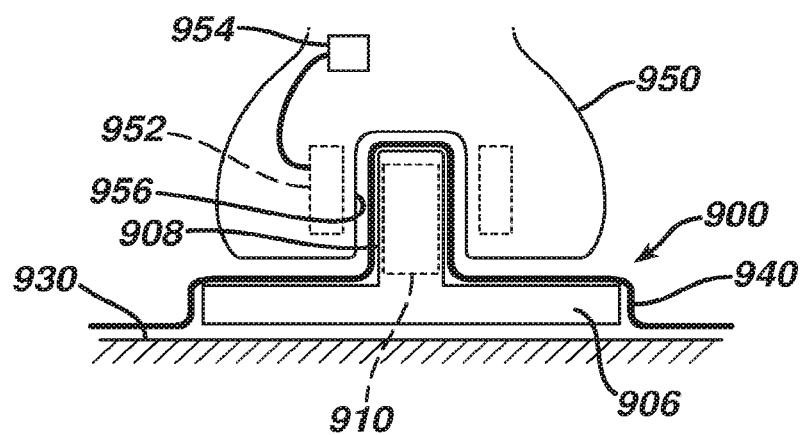
FIG. 19 depicts a partial cross-sectional view of the charging peg system of FIG. 18, including a coupled medical device.

FIGS. 18-19 depict another exemplary use of a sterile drape and inductive charging device. In particular, FIGS. 18-19 show an inductive charging device (900) on a mayo stand (930), with a sterile drape (940) laid over inductive charging device (900). Inductive charging device (900) of this example includes a cable (902) that is configured to plug into a conventional wall outlet (904), a base portion (906), an upright peg portion (908), and a primary coil (910). Primary coil (910) is shown in FIG. 19 as being located within upright peg portion (908), though it should be understood that primary coil (910) may be located elsewhere. For instance, in some other versions, primary coil (910) is located in base portion (906) (e.g., coaxial with upright peg portion (908), etc.).

Charging device (900) of this example is configured for use with a medical device having a handpiece (950) as shown in FIG. 19. In particular, handpiece (950) includes a secondary coil (952), which is in communication with an integral power source (954) in handpiece (950). The bottom of handpiece (950) defines a recess (956) that is configured to receive upright peg portion (908) of charging device (900). Upright peg portion (908) and recess (956) thus cooperate to assist in properly positioning coils (910, 952) relative to each other. Upright peg portion (908) also provides some degree of structural support to handpiece (950) (e.g., reducing the likelihood of handpiece (950) tipping over, etc.). When coils (910, 952) are properly positioned within sufficient proximity of each other, coils (910, 952) inductively couple, forming a transformer and charging power source (954). Sterile drape (940) conforms to the interface between handpiece (950) and charging device (900), this maintaining the sterile barrier between these components while also permitting inductive charging to occur therethrough.

As with charging pad (800), charging device (950) may be used in an operating room without being sterile and without compromising the sterility of handpiece (950) or other items in the operating room. In other words, even if charging device (900) is non-sterile, power source (954) may be charged by charging device (900) through sterile drape (940), and sterile drape (940) may help maintain the sterility of handpiece (950) by preventing contamination from non-sterile charging device (900). The medical device having handpiece (950) may be constructed and operable in accordance with medical device (10, 100) and/or in accordance with at least some of the teachings of any of the references cited herein. Various other types of devices that may include handpiece (950) will be apparent to those of ordinary skill in the art in view of the teachings herein. Similarly, various other suitable forms that charging device (900) may take will be apparent to those of ordinary skill in the art in view of the teachings herein.

VI. Exemplary Medical Device Powered by Supercapacitor

Figure 20:
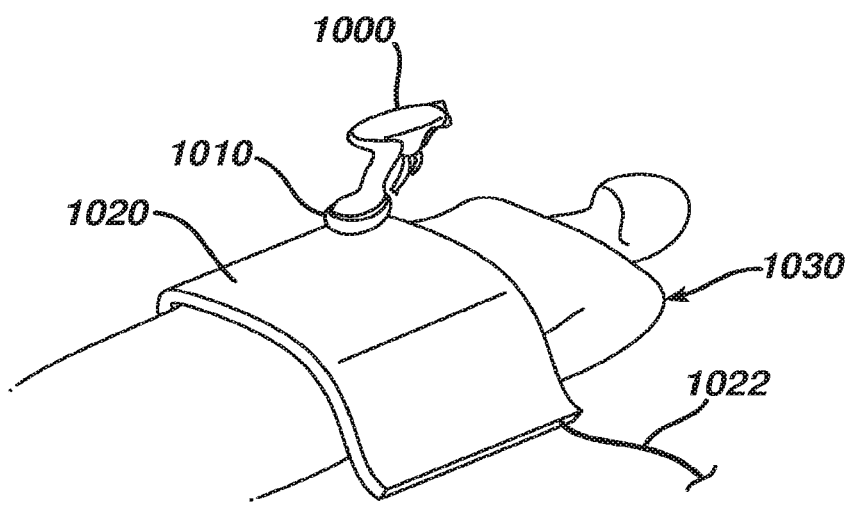
FIG. 20 depicts an exemplary medical device powered by supercapacitors, with a charging pad draped over a patient.

While several of the examples described above have included batteries as a primary integral source of power in a medical device, it should be understood that other types of components may provide a primary integral source of power in a medical device. For instance, FIG. 20 shows a medical device (1000) having an integral power source (1010) that comprises one or more supercapacitors, also known as electric double-layer capacitors (EDLCs). Medical device may otherwise be constructed and operable in accordance with medical device (10, 100) and/or in accordance with at least some of the teachings of any of the references cited herein. It should be understood that one or more supercapacitors of power source (1010) may provide sufficient power to perform one or more operational acts with medical device (1000) (e.g., one or more transections with an end effector of medical device (1000), etc.). However, the power provided by supercapacitors of power source (1010) may be more in the form of short bursts as compared to the power delivery that might be expected from conventional batteries. It therefore might be warranted in some instances to provide relatively immediate recharging of power source (1010).

FIG. 20 also shows a charging pad (1020) draped directly over the torso of a patient (1030). Charging pad (1020) includes a power cable (1022) that is configured to plug into a conventional wall outlet or piece of capital equipment, etc. Charging pad (1020) is further configured to charge power source (1010) through inductive coupling or otherwise. Due to the nature of supercapacitors, the charging of power source (1010) may be much faster than the charge time that might otherwise be expected with conventional rechargeable batteries. Thus, in the present example, a surgeon may repeatedly place medical device (1000) on or at least directly over charging pad (1020) as many times as needed to keep power source (1010) sufficiently charged during a medical procedure. Charging pad (1020) may be sterilized before use; or may have a sterile drape placed over it (and under it) to avoid contaminating medical device (1000) (and patient (1030)). It should also be understood that charging pad (1020) may be placed anywhere, and need not necessarily be draped over patient (1030). It should also be understood that medical device (1000) may include a magnet or other feature that helps keep medical device (1000) upright (e.g., to avoid tipping over, etc.) when medical device (1000) is plaled on charging pad (1020). Various other suitable ways in which supercapacitors may be incorporated into a medical device will be apparent to those of ordinary skill in the art in view of the teachings herein. It should also be understood that, in any example mentioned herein that includes one or more batteries, such batteries may be replaced or supplemented with a capacitor, supercapacitor, and/or other type of power source.

VII. Conclusion

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A medical system, comprising:
   (a) a medical device, including:
      (i) a housing,
      (ii) an integral power source positioned within the housing,
      (iii) an active element in communication with the integral power source, wherein the active element is operable to perform an operation on a tissue of a patient,
      (iv) a recess, and
      (v) a first charging feature positioned within the housing in communication with the integral power source;
   (b) a charging device including a second charging feature, wherein the charging device is configured to communicate with the integral power source of the medical device to thereby charge the integral power source of the medical device when the first charging feature is aligned with the second charging feature, wherein the charging device further includes a base portion and a peg portion extending upwardly from the base portion, wherein the recess of the medical device is configured to receive the peg portion of the charging device such that the peg portion supports the medical device thereon in a predetermined alignment thereby reducing the likelihood of the medical device moving relative to the charging device for supporting the medical device in the predetermined alignment while charging the integral power source of the medical device; and (c) a sterile barrier having a flexible portion interposed between the first charging feature within the housing and the second charging feature of the charging device, wherein the sterile barrier is configured to permit the second charging feature of the charging device to establish contact with the first charging feature of the medical device without compromising sterility of exterior portions of the medical device.

2. The medical system of claim 1, wherein the first charging feature of the medical device includes a first coil, wherein the second charging feature of the charging device includes a second coil, wherein the first and second coils are configured to establish an inductive coupling to charge the integral power source.

3. The medical system of claim 1, wherein the first charging feature of the medical device includes a first coil positioned about the recess, wherein the second charging feature of the charging device includes a second coil positioned within the peg portion, wherein the first and second coils are configured to establish an inductive coupling to charge the integral power source when the peg portion is received within the recess.

4. The medical system of claim 1, wherein the sterile barrier includes a flexible drape configured to conform to the interface between the medical device and the charging device.

5. The medical system of claim 1, wherein the integral power source includes a battery.

6. The medical system of claim 1, wherein the integral power source includes a supercapacitor.

7. The medical system of claim 1, wherein the active element includes an ultrasonic blade or an RF electrode.

8. The medical system of claim 1, wherein the charging device includes a cable configured to be plugged into an electrical outlet to supply power to the second charging feature.

9. The medical system of claim 1, wherein the medical device further includes a control module in communication with the first charging feature, wherein the charging device further includes a control module in communication with the second charging feature, wherein the control modules are configured to provide data communication along a waveform communicated between the first charging feature and the second charging feature.

10. The medical system of claim 9, wherein the waveform further communicates power from the second charging feature to the first charging feature such that the data communication is superimposed on the power communication.

11. The medical system of claim 1, wherein the second charging feature is within the peg portion of the charging device, and wherein the flexible portion is interposed between the first charging feature within the housing and the peg portion of the charging device.

12. A medical system, comprising:
(a) a charging device including a primary coil;
(b) a medical device, including:
  (i) a housing,
  (ii) an integral power source positioned within the housing,
  (iii) an active element in communication with the integral power source, wherein the active element is operable to perform an operation on a tissue of a patient, and
  (iv) a secondary coil positioned within the housing in communication with the integral power source; and
(c) a sterile barrier interposed between the housing and the charging device, wherein the sterile barrier includes a flexible drape interposed between secondary coil within the housing and the primary coil of the charging device and configured to conform to the interface between the medical device and the charging device;
wherein the primary and secondary coils are configured to establish an inductive coupling to charge the integral power source;
wherein the charging device is configured to receive the medical device such that the primary coil receives the secondary coil therein for aligning primary and secondary coils in a predetermined alignment and supporting medical device while charging the integral power source; and
wherein the sterile barrier is configured to permit the primary coil of the charging device to establish contact with the secondary coil of the medical device without compromising sterility of exterior portions of the medical device.

13. The medical system of claim 12, wherein the primary coil of the charging device is positioned within a peg portion of the charging device, wherein the secondary coil of the medical device is positioned about a recess of the housing, wherein the peg portion is configured to be received within the recess to establish the inductive coupling.

14. The medical system of claim 13, wherein the peg portion is configured to support the medical device when the peg portion is received within the recess to thereby reduce the likelihood of the medical device moving relative to the charging device.

15. The medical system of claim 12, wherein the sterile barrier includes a flexible drape configured to conform to the interface between the medical device and the charging device.

16. The medical system of claim 12, wherein the active element includes an ultrasonic blade or an RF electrode.

17. The medical system of claim 12, wherein the primary coil defines a primary axis such that the primary coil surrounds the primary axis, wherein the secondary coil defines a secondary axis such that the secondary coil surrounds the secondary axis, and wherein the charging device is configured to receive the medical device such that the primary axis coaxially aligns with the secondary axis in the predetermined alignment.

18. A medical system, comprising:
(a) a medical device, including:
  (i) a housing,
  (ii) an integral power source positioned within the housing, wherein the integral power source includes a supercapacitor,
  (iii) an active element in communication with the integral power source, wherein the active element is operable to perform an operation on a tissue of a patient, and
  (iv) a first charging feature defining a first axis and positioned within the housing in communication with the integral power source;
(b) a charging device including a second charging feature defining a second axis, wherein the charging device is configured to communicate with the integral power source of the medical device to thereby charge the integral power source of the medical device when the first axis of the first charging feature is coaxially aligned with second axis of the second charging feature in a predetermined alignment; and (c) a sterile barrier interposed between the housing and the charging device, wherein the sterile barrier is configured to permit the second charging feature of the charging device to establish contact with the first charging feature of the medical device without compromising sterility of exterior portions of the medical device, wherein the sterile barrier includes a flexible drape interposed between the first charging feature within the housing and the second charging feature of the charging device and configured to conform to the interface between the medical device and the charging device.

19. The medical system of claim 18, wherein the active element includes an ultrasonic blade or an RF electrode.

20. The medical system of claim 18, wherein the first axis extends along the second axis in the predetermined alignment.

\* \* \* \* \*